United States Patent [19]

Himmelsbach et al.

[11] Patent Number: 5,463,071

[45] Date of Patent: Oct. 31, 1995

[54] 5-MEMBERED HETEROCYCLIC COMPOUNDS, PROCESSES FOR PREPARING THEM AND PHARMACEUTICAL COMPOSITIONS CONTAINING THESE COMPOUNDS

[75] Inventors: Frank Himmelsbach; Guenter Linz, both of Mittelbiberach; Volkhard Austel, Biberach; Helmut Pieper, Biberach; Thomas Mueller, Biberach; Johannes Weisenberger, Biberach; Elke Seewaldt-Becker, Biberach, all of Germany

[73] Assignee: Dr. Karl Thomae GmbH, Biberach an der Riss, Germany

[21] Appl. No.: 148,724

[22] Filed: Nov. 8, 1993

Related U.S. Application Data

[63] Continuation of Ser. No. 919,343, Jul. 23, 1992, abandoned.

[30] Foreign Application Priority Data

Jul. 27, 1991 [DE] Germany .................. 41 24 942.9

[51] Int. Cl.⁶ .................. C07D 257/02; C07D 257/06
[52] U.S. Cl. .................. 548/251; 548/111; 548/254; 546/21; 546/22; 546/268; 546/283; 544/122; 544/232; 544/238; 544/243

[58] Field of Search .................. 548/111, 253, 548/251, 254, 251; 546/21, 22, 268, 283; 544/232, 238, 243, 122

[56] References Cited

U.S. PATENT DOCUMENTS

| 4,886,885 | 12/1989 | Baker et al. | 548/253 |
|---|---|---|---|
| 5,081,127 | 1/1992 | Carini | 514/359 |

*Primary Examiner*—Mukund J. Shah
*Assistant Examiner*—Pavanaram K. Sripada
*Attorney, Agent, or Firm*—Robert P. Raymond; Alan R. Stempel; Mary-Ellen Devlin

[57] ABSTRACT

Compounds of the formula

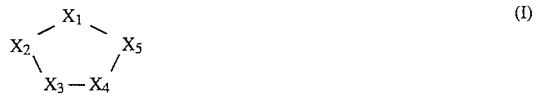

wherein $X_1$ to $X_5$ are as defined herein, the tautomers, the stereoisomers including the mixtures thereof and the salts thereof, particularly the physiologically acceptable salts thereof with inorganic or organic acids or bases. The compounds are useful for inhibiting undesirable cell aggregation.

12 Claims, No Drawings

5-MEMBERED HETEROCYCLIC COMPOUNDS, PROCESSES FOR PREPARING THEM AND PHARMACEUTICAL COMPOSITIONS CONTAINING THESE COMPOUNDS

This is a continuation of application Ser. No. 919,343, filed Jul. 23, 1992, now abandoned.

The invention relates to 5-membered heterocyclic compounds of general formula

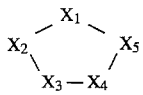 (I)

the tautomers thereof, the stereoisomers thereof, including the mixtures thereof and the salts thereof, particularly the physiologically acceptable salts thereof with inorganic or organic acids or bases, which have valuable pharmacological properties, preferably aggregation-inhibiting effects, pharmaceutical compositions containing these compounds and processes for preparing them.

In general formula I above, with the proviso that the 5-membered heterocyclic ring does not represent a pyrrolidine, pyrroline, pyrrolinone or pyrrolidinone ring and contains at least one carbon atom, one of the groups $X_1$ to $X_5$ represents a group of the formula

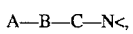

wherein

A represents a cyano group, a straight-chained or branched cyanoalkyl group having a total of 2 to 4 carbon atoms, an amino group which is not directly bound to a phenyl ring of groups B or C, a straight-chained or branched $C_{1-4}$-aminoalkyl group, an amidino or guanidino group, whilst in each of the above-mentioned amino, aminoalkyl, amidino or guanidino groups, at one of the nitrogen atoms one or two hydrogen atoms may be replaced by one or two $C_{1-4}$-alkyl groups or a hydrogen atom may be replaced by a $C_{2-5}$-(alkoxycarbonyl) group, by a $C_{4-6}$-(alkenyloxycarbonyl) group, by an aralkoxycarbonyl, arylcarbonyl, aryloxycarbonyl, alkanoyloxymethoxy-carbonyl, cycloalkanoyloxymethoxycarbonyl, aralkanoyloxymethoxycarbonyl, aroyloxymethoxycarbonyl, phosphono, dialkylphosphoryl or O-alkylphosphono group, wherein the alkanoyl moieties may each contain a total of 2 to 7 carbon atoms and the cycloalkanoyl moieties may contain a total of 4 to 8 carbon atoms, and each methoxy moiety may be substituted by a $C_{3-6}$-cycloalkyl group, by an aralkyl, aryl or alkyl group or by two alkyl groups which together with the methylene carbon atom may also form a 5- or 6-membered ring, or, if B or B and C together represent a cyclic imine with 4 to 7 ring members, A may also represent a hydrogen atom bound to the imino nitrogen or an alkyl group bound to the imino nitrogen, B represents a bond,
an alkylene or alkenylene group,
a phenylene group which may be mono-or disubstituted by fluorine, chlorine or bromine atoms, by $C_{1-4}$-alkyl groups, by trifluoromethyl, hydroxy, alkoxy, alkylsulphenyl, alkylsulphinyl, alkylsulphonyl, nitro, $(R_1)_2N—$, $(R_1)_2NCO—$ or $(R_1)_2NSO_2—$ groups or by $R_1NH—$ groups substituted by an alkylcarbonyl, aralkylcarbonyl, arylcarbonyl, heteroarylcarbonyl, alkylsulphonyl, aralkylsulphonyl or arylsulphonyl group, wherein the substituents may be identical or different and $R_1$ may represent a hydrogen atom, a $C_{1-5}$-alkyl group, an aralkyl, aryl or heteroaryl group in each case, a pyridinylene, pyrimidinylene, pyrazinylene, pyridazinylene or triazinylene group which may each be substituted in the carbon skeleton by a chlorine atom or by an alkyl or alkoxy group, whilst additionally one or two $—CH=N—$ groups may each be replaced by a $—CO—NR_1—$ group and then one of the nitrogen atoms may be bound to the group C instead of to the group $R_1$, a cyclopropylene group optionally substituted by an alkyl, aralkyl or aryl group, a $C_{4-5}$-cycloalkylene group optionally substituted by an alkyl, aralkyl or aryl group, wherein a CH unit may be replaced by a nitrogen atom and additionally a methylene group adjacent to the nitrogen atom may be replaced by a carbonyl group, a $C_{6-7}$-cycloalkylene group optionally substituted by an alkyl, aralkyl or aryl group, wherein one or two CH units may each be replaced by a nitrogen atom, and additionally one or two methylene groups adjacent to a nitrogen atom may be replaced by a carbonyl group, and C represents a phenylene group which may be mono- or disubstituted by fluorine, chlorine or bromine atoms, by $C_{1-4}$-alkyl groups, by trifluoromethyl, hydroxy, alkoxy, alkylsulphenyl, alkylsulphinyl, alkylsulphonyl, nitro, $(R_1)_2N—$, $(R_1)_2NCO—$ or $(R_1)_2NSO_2—$ groups or by $R_1NH—$ groups substituted by an alkylcarbonyl, aralkylcarbonyl, arylcarbonyl, heteroarylcarbonyl, alkylsulphonyl, aralkylsulphonyl or arylsulphonyl group, wherein the substituents may be identical or different, an indanylene or 1,2,3,4-tetrahydronaphthylene group wherein the saturated ring is bound to the group A or B and the aromatic ring is bound to the atom of the group $X_1$ to $X_5$ situated in the ring, a pyridinylene, pyrimidinylene, pyrazinylene, pyridazinylene or triazinylene group, each of which may be substituted in the carbon skeleton by a chlorine atom or by an alkyl or alkoxy group, whilst additionally one or two $—CH=N—$ groups may each be replaced by a $—CO—NR_1—$ group and then one of the nitrogen atoms, instead of being bound to the group $R_1$, may also be bound to the group B or to the atom of the group $X_1$ to $X_5$ situated in the ring, but C cannot represent a pyrimidinylene group if the heterocyclic ring system denotes a dithiolane ring and at the same time the group A denotes an amino group, a $C_{4-5}$-cycloalkylene group optionally substituted by an alkyl, aralkyl or aryl group, wherein a CH unit may be replaced by a nitrogen atom and additionally a methylene group adjacent to the nitrogen atom may be replaced by a carbonyl group, or a $C_{6-7}$-cycloalkylene group optionally substituted by an alkyl, aralkyl or aryl group, wherein one or two CH units may each be replaced by a nitrogen atom, whilst additionally one or two methylene groups adjacent to a nitrogen atom may be replaced by a carbonyl group, a second of the groups $X_1$ to $X_5$ represents a group of the formula

F—E—D—N<,

F—E—D—CH< or

F—E—D—C≡ wherein D represents a straight-chained or branched alkylene or alkenylene group optionally substituted by a hydroxy, alkoxy, alkylsulphenyl, $(R_1)_2N$—, (alkylcarbonyl)$NR_1$—, (aralkylcarbonyl)$NR_1$—, (arylcarbonyl)$NR_1$—, (heteroarylcarbonyl)$NR_1$—, (alkoxycarbonyl)$NR_1$—, (aralkoxycarbonyl)$NR_1$—, (aryloxycarbonyl)$NR_1$—, $((R_1)_2NCO)NR_1$—, (alkylsulphonyl)$NR_1$—, (aralkylsulphonyl)$NR_1$—, (arylsulphoneyl)$NR_1$— or $R_1OCO$— group, wherein each alkylene moiety may contain 1 to 5 carbon atoms and each alkenylene moiety may contain 2 to 5 carbon atoms, a phenylene group which may be mono- or disubstituted by fluorine, chlorine or bromine atoms, by $C_{1-4}$-alkyl groups, by trifluoromethyl, hydroxy, alkoxy, alkylsulphenyl, alkylsulphinyl, alkylsulphonyl, nitro, $(R_1)_2N$—, $(R_1)_2NCO$—, $(R_1)_2NSO_2$— or $R_1OCO$— alkoxy groups or by $R_1NH$ groups substituted by an alkylcarbonyl, aralkylcarbonyl, arylcarbonyl, heteroarylcarbonyl, alkylsulphonyl, aralkylsulphonyl or arylsulphonyl group, wherein the substituents may be identical or different, a pyridinylene, pyrimidinylene, pyrazinylene, pyridazinylene or triazinylene group, each of which may be substituted in the carbon skeleton by a chlorine atom or by an alkyl or alkoxy group, whilst additionally one or two —CH=N— groups may each be replaced by a —CO—$NR_1$— group and then one of the nitrogen atoms, instead of being bound to the group $R_1$, may also be bound to the group E, provided that this does not represent a bond and is not bonded to the group D via an oxygen or sulphur atom, or it may be bound to the atom of the group $X_1$ to $X_5$ situated in the ring, a $C_{4-5}$-cycloalkylene group optionally substituted by an alkyl, aralkyl or aryl group, wherein a CH unit may be replaced by a nitrogen atom and additionally a methylene group adjacent to the nitrogen atom may be replaced by a carbonyl group, a $C_{6-7}$-cycloalkylene group optionally substituted by an alkyl, aralkyl or aryl group, wherein one or two CH units may be replaced by a nitrogen atom, whilst additionally one or two methylene groups adjacent to a nitrogen atom may be replaced by a carbonyl group, or a $C_{1-6}$-alkylene group linked via the group $W_1$ to the atom of the group $X_1$ to $X_5$ located in the ring, wherein $W_1$ represents an $NR_1$— group or an oxygen or sulphur atom, E represents a bond, a straight-chained or branched $C_{1-5}$-alkylene group or a $C_{2-5}$-alkenylene group which may each be substituted by an $R_1OCO$-alkyl group, or an alkylene group linked via the group $W_2$ to the group D, wherein $W_2$ represents an oxygen or sulphur atom, a sulphinyl, sulphonyl, —$NR_1$—, -(alkylcarbonyl)N—, -(aralkylcarbonyl)N—, -(arylcarbonyl)N—, -(heteroarylcarbonyl)N—, -(alkylsulphonyl)N—, -(arylsulphonyl)N—, —$CONR_1$— or —$NR_1CO$— group, F represents a carbonyl group which is not bound to a heteroatom of groups D or E, which may be substituted by a hydroxy group, by an amino group, by a $C_{1-6}$-alkoxy group (in which a $C_{1-3}$-alkoxy moiety may be substituted in the 1-, 2- or 3-position by a $C_{4-8}$-cycloalkyl group, by an aryl or heteroaryl group or in the 2- or 3-position may be substituted by a pyrrolidin-2-on-1-yl, morpholino, thiomorpholino or 1-oxidothiomorpholino group, by a $C_{4-8}$-cycloalkoxy group, by an alkanoyloxy-methoxy group having a total of 2 to 7 carbon atoms in the alkanoyl moiety, by a cycloalkanoyloxymethoxy group having a total of 4 to 8 carbon atoms in the cycloalkanoyl moiety, by an alkoxycarbonyloxymethoxy group having 1 to 6 carbon atoms in the alkyl moiety, by a cycloalkoxycarbonyloxymethoxy group having 3 to 7 carbon atoms in the cycloalkyl moiety, or by an aroyloxymethoxy, aralkanoyloxymethoxy, aryloxycarbonyloxymethoxy or aralkoxycarbonyloxymethoxy group wherein the methoxy moiety may be substituted by a $C_{1-6}$-alkyl group, by a $C_{3-7}$-cycloalkyl group or by an aralkyl or aryl group, or F may represent a sulpho-, phosphono-, O-alkylphosphono- or tetrazol-5-yl group, whilst if A represents an amino group or a cyano group, the shortest distance between this group and the group F is at least 10 bonds and generally A cannot represent a cyano group if the heterocyclic ring system represents a pyrazoline ring and at the same time the groups C and D represent unsubstituted phenylene groups and at the same time the groups B and E represent a bond or if the heterocyclic ring system represents an oxazole or oxazoline ring, and at the same time the group C represents an unsubstituted phenylene group and B represents a bond, a third of the groups $X_1$ to $X_5$ represents a sulphur atom, a sulphinyl, sulphonyl, $R_1N$<, $R_2C$≡ or $(R_2)_2C$< group or an N-atom, wherein $R_1$ is defined as hereinbefore and $R_2$ represents a hydrogen, chlorine or bromine atom, a $C_{1-7}$-alkyl group, an arylalkyl, aryl, heteroaryl, alkoxy, $(R_1)_2N$—, $R_1OOC$— or $(R_1)_2NCO$— group, a fourth of the groups $X_1$ to $X_5$ represents an oxygen, sulphur or nitrogen atom, a sulphonyl or $R_2C$≡ group or a carbonyl group, if the latter is not between two nitrogen atoms, a fifth of the groups $X_1$ to $X_5$ represents a nitrogen atom, an $R_2C$≡ or $(R_2)_2C$< group or two adjacent groups of the groups $X_1$ to $X_5$ together represent an o-phenylene group, whilst unless otherwise stated the above-mentioned alkyl, alkylene, alkenylene or alkoxy moieties may each contain 1 to 3 carbon atoms, and the above-mentioned terms "an aryl group" or "an aroyl group" denote a phenyl, naphthyl or benzoyl group which may be monosubstituted by a trifluoromethyl, carboxy, $(R_1)_2NCO$—, alkoxycarbonyl-, alkylcarbonyl-, alkylsulphenyl-, alkylsulphinyl-, alkylsulphonyl-, nitro-, $(R_1)_2N$—, alkylcarbonyl-$NR_1$—, aralkylcarbonyl-$NR_1$—, arylcarbonyl-$NR_1$—, heteroarylcarbonyl-$NR_1$—, alkylsulphonyl-$NR_1$—, aralkylsulphonyl-$NR_1$—, arylsulphonyl-$NR_1$— or $(R_1)_2N$-sulphonyl-group or may be mono-, di- or trisubstituted by fluorine, chlorine or bromine atoms or by hydroxy, alkoxy or $C_{1-4}$-alkyl groups, and the above-mentioned term "a heteroaryl group" denotes a 5-membered heteroaromatic ring which contains an oxygen, sulphur or nitrogen atom, a nitrogen atom and an oxygen, sulphur or nitrogen atom or two nitrogen atoms and an oxygen, sulphur or nitrogen atom or a 6-membered heteroaromatic ring which contains one, two or three nitrogen atoms and wherein, additionally, one or two —CH═N— groups may be replaced by a —CO—NR$_1$— group, whilst the above-mentioned heteroaromatic rings may additionally be substituted by one or two alkyl groups or by a fluorine, chlorine or bromine atom or by a hydroxy or alkoxy group.

Thus, the above-mentioned general formula I includes, for example, the correspondingly substituted furan, tetrahydrofuran, 2,3-dihydro-furan, 2,5-dihydro-furan, thiophene, 2,3-dihydrothiophene, 2,5-dihydro-thiophene, tetrahydrothiophene, S-oxidotetrahydrothiophene, S,S,dioxidotetrahydrothiophene, 1,2-dithiolan, 1,3-dithiolan, 1,3-dithiolan-S,S,S',S'-tetraoxide, pyrrole, indole, isoindole, 2,3-dihydro-indole, 2,3-dihydroisoindole, 2-indolone, imidazole, 4,5-dihydro-imidazole, tetrahydroimidazole, benzimidazoline, pyrazole, 2H-pyrazol-5-one, 4,5-dihydropyrazole, 1,5-dihydro-pyrazole, 2,3-dihydro-indazole, oxazole, isoxazole, oxazoline, oxazolidine, thiazole, isothiazole, thiazoline, thiazolidine, 1,3,4-oxadiazole, 1,3,4-thiadiazole, 1,2,3-triazole, 1,2,4-triazole and tetrazole derivatives.

Preferred compounds of general formula I are those wherein, with the proviso that the 5-membered heterocyclic ring does not represent a pyrrolidine, pyrroline, pyrrolinone or pyrrolidinone ring and contains at least one carbon atom, one of the groups $X_1$ to $X_5$ represents a group of the formula

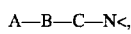

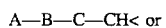

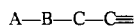

wherein A represents a cyano group, a straight-chained or branched cyanoalkyl group having a total of 2 to 4 carbon atoms, an amino group which is not directly bound to a phenyl ring of group B or C, a straight-chained or branched $C_{1-4}$-aminoalkyl group, an amidino or guanidino group, whilst in each of the above-mentioned amino, aminoalkyl, amidino or guanidino groups, at one of the nitrogen atoms one or two hydrogen atoms may be replaced by one or two $C_{1-4}$-alkyl groups or a hydrogen atom may be replaced by an alkoxycarbonyl group having a total of 2 to 5 carbon atoms, by an alkenyloxycarbonyl group having a total of 4 or 5 carbon atoms, by an aralkoxycarbonyl, aryloxycarbonyloxy or arylcarbonyl group, by a phosphono, dialkylphosphoryl or O-alkylphosphono group, or by an alkanoyloxymethoxycarbonyl group, wherein the alkanoyl moiety may contain a total of 2 to 7 carbon atoms and the methoxy moiety may be substituted by an alkyl group, or if B or B and C together represent a cyclic imine having 6 ring members, A may also represent a hydrogen atom bound to the imino nitrogen or an alkyl group bound to the imino nitrogen, B represents a bond, a phenylene group which may be mono- or disubstituted by fluorine, chlorine or bromine atoms, by $C_{1-4}$-alkyl groups, by trifluoromethyl, hydroxy, alkoxy, alkylsulphenyl, alkylsulphinyl, alkylsulphonyl, nitro, $(R_1)_2N$—, $(R_1)_2NCO$— or $(R_1)_2NSO_2$— groups or by $R_1NH$— groups substituted by an alkylcarbonyl, aralkylcarbonyl, arylcarbonyl, heteroarylcarbonyl, alkylsulphonyl, aralkylsulphonyl or arylsulphonyl group, wherein the substituents may be identical or different and R represents a hydrogen atom, a $C_{1-5}$-alkyl group, an aralkyl or aryl group, a pyridinylene, pyrimidinylene, pyrazinylene or pyridazinylene group, each of which may be substituted in the carbon skeleton by an alkyl group, whilst additionally one or two —CH═N— groups may each be replaced by a —CO—NR$_1$— group and then one of the nitrogen atoms, instead of being bound to the group $R_1$, may also be bound to the group C, a $C_{3-5}$-cycloalkylene group, a cyclohexylene group wherein one or two CH units may each be replaced by a nitrogen atom, whilst additionally one or two methylene groups adjacent to a nitrogen atom may be replaced by a carbonyl group, and C represents a phenylene group which may be mono- or disubstituted by fluorine, chlorine or bromine atoms, by $C_{1-4}$-alkyl groups, by trifluoromethyl, hydroxy, alkoxy, alkylsulphenyl, alkylsulphinyl, alkylsulphonyl, nitro, $(R_1)_2N$—, $(R_1)_2NCO$— or $(R_1)_2NSO_2$— groups substituted by an alkylcarbonyl, aralkylcarbonyl, arylcarbonyl, heteroarylcarbonyl, alkylsulphonyl, aralkylsulphonyl or arylsulphonyl group, wherein the substituents may be identical or different, an indanylene or 1,2,3,4-tetrahydronaphthylene group wherein the saturated ring is bound to the group A and the aromatic ring is bound to the atom of the group $X_1$ to $X_5$ located in the ring, a pyridinylene, pyrimidinylene, pyrazinylene or pyridazinylene group, each of which may be alkyl-substituted in the carbon skeleton, whilst additionally one or two —CH═N— groups may be replaced by a —CO—NR$_1$— group and then one of the nitrogen atoms, instead of being bound to the group $R_1$, may also be bound to the group B or to the atom of the group $X_1$ to $X_5$ located in the ring, provided that this is a carbon atom, a cyclohexylene group wherein one or two CH units may each be replaced by a nitrogen atom, and in which additionally one or two methylene groups adjacent to a nitrogen atom may be replaced by a carbonyl group, a second of the groups $X_1$ to $X_5$ denotes a group of the formula

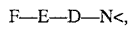

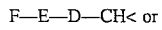

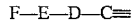

wherein D represents a straight-chained or branched alkylene or alkenylene group, optionally substituted by a hydroxy, alkoxy, alkylsulphenyl, $(R_1)_2N$—, (alkylcarbonyl)NR$_1$—, (aralkylcarbonyl)NR$_1$—, (arylcarbonyl)NR$_1$—, (heteroarylcarbonyl)NR$_1$—, (alkoxycarbonyl)NR$_1$—, (aralkoxycarbonyl)NR$_1$—, ((R$_1$)$_2$NCO)NR$_1$—, (alkylsulphonyl)NR$_1$—, (aralkylsulphonyl)NR$_1$—, (arylsulphonyl)NR$_1$— or R$_1$OCO— group wherein the alkylene moiety may contain 1 to 5 carbon atoms and the alkenylene moiety may contain 2 to 5 carbon atoms, a phenylene group which may be mono- or disubstituted by fluorine, chlorine or bromine atoms, by $C_{1-4}$-alkyl groups, by trifluoromethyl, hydroxy, alkoxy, alkylsulphenyl, alkylsulphinyl, alkylsulphonyl, nitro, $(R_1)_2N$—, $(R_1)_2NCO$—, $(R_1)_2NSO_2$— or $R_1OCO$-alkoxy groups or by $R_1NH$— groups substituted by an alkylcarbonyl, aralkylcarbonyl, arylcarbonyl, heteroarylcarbonyl, alkylsulphonyl, aralkylsulphonyl or arylsulphonyl group, whilst the substituents may be identical or different, a pyridinylene, pyrimidinylene, pyrazinylene or pyridazinylene group, each of which may be substituted by an alkyl group in the carbon skeleton, whilst additionally one or two —CH=N— groups may each be replaced by a —CO—NR$_1$— group and then one of the nitrogen atoms, instead of being bound to the group $R_1$, may also be bound to the group E, provided that this is not a bond and is not bound via a heteroatom to the group D, or it may be bound to the atom of the particular group $X_1$ to $X_5$ located in the ring, provided that the latter is a carbon atom, a cyclohexylene group wherein one or two CH units may each be replaced by a nitrogen atom, and additionally one or two methylene groups adjacent to a nitrogen atom may each be replaced by a carbonyl group, or a $C_{1-3}$-alkylene group linked via the group $W_1$ to the atom of the particular group $X_1$ to $X_5$ located in the ring, provided that the latter is a carbon atom, wherein $W_1$ represents an $NR_1$ group or an oxygen or sulphur atom, E denotes a bond, a straight-chained or branched $C_{1-5}$-alkylene group or a $C_{2-5}$-alkenylene group, each of which may be substituted by one or two $R_1OCO$-alkyl groups, or an alkylene group linked via the group $W_2$ to the group D, wherein $W_2$ denotes an oxygen or sulphur atom or a sulphinyl, sulphonyl, —NR$_1$—, -(alkylcarbonyl)N—, -(aralkylcarbonyl)N—, -(arylcarbonyl)N—, -(heteroarylcarbonyl)N—, -(alkylsulphonyl)N—, -(arylsulphonyl)N—, —CONR$_1$— or —NR$_1$CO— group and is not bound to a heteroatom of group D, F represents a carbonyl group which is not bound to a heteroatom of groups D or E but which is substituted by a hydroxy group, by an amino group, by a $C_{1-5}$-alkoxy group (wherein a $C_{1-3}$-alkoxy moiety may be substituted in the 1-, 2- or 3-position by a $C_{5-7}$-cycloalkyl group, by an aryl or heteroaryl group or, in the 2- or 3-position, by a pyrrolidin-2-on-1-yl, morpholino, thiomorpholino or 1-oxido-thiomorpholino group), by a $C_{4-8}$-cycloalkoxy group, by an alkanoyloxymethoxy group having a total of 2 to 7 carbon atoms in the alkanoyl moiety, by an aroyloxymethoxy group, by an alkoxycarbonyloxymethoxy group having 1 to 4 carbon atoms in the alkyl moiety or by a cycloalkoxy-carbonyloxymethoxy group having 5 to 6 carbon atoms in the cycloalkyl moiety, wherein each methoxy moiety may be substituted by an alkyl group, or F represents a sulpho, phosphono, O-alkylphosphono or tetrazol-5-yl group, whilst if A represents an amino group or a cyano group the shortest distance between this group and the group F is at least 10 bonds and generally A cannot denote a cyano group if the heterocyclic ring system is a pyrazoline ring and at the same time the groups C and D denote unsubstituted phenylene groups and simultaneously the groups B and E denote a bond or, if the heterocyclic ring system is an oxazole or oxazoline ring and at the same time the group C denotes an unsubstituted phenylene group and B is a bond, a third of the groups $X_1$ to $X_5$ denotes an $R_1N<$, $R_2C\equiv$ or $(R_2)_2C<$ group or an N-atom, wherein $R_1$ is defined as hereinbefore, and $R_2$ denotes a hydrogen, chlorine or bromine atom, a $C_{1-7}$-alkyl group, an arylalkyl, aryl, heteroaryl, alkoxy, $(R_1)_2N$—, $R_1OOC$— or $(R_1)_2NCO$— group, a fourth of the groups $X_1$ to $X_5$ denotes an oxygen, sulphur or nitrogen atom or an $R_2C\equiv$ group or a carbonyl group, provided that the latter is not situated between two nitrogen atoms, a fifth of the groups $X_1$ to $X_5$ denotes a nitrogen atom, an $R_2C\equiv$ or $(R_2)_2C<$ group or two adjacent groups of groups $X_1$ to $X_5$ together denote an o-phenylene group, the tautomers, the stereoisomers including the mixtures thereof and the salts thereof, particularly the physiologically acceptable salts thereof with inorganic or organic acids or bases, whilst unless otherwise specified the above-mentioned alkyl, alkylene, alkenylene or alkoxy moieties may each contain 1 to 3 carbon atoms, and by the terms "an aryl group" or "an aroyl group" mentioned hereinbefore is meant a phenyl, naphthyl or benzoyl group which may be monosubstituted by a trifluoromethyl, carboxy, $(R_1)_2NCO$—, alkoxycarbonyl, alkylcarbonyl, alkylsulphenyl, alkylsulphinyl, alkylsulphonyl, nitro, $(R_1)_2N$—, alkylcarbonyl-NR$_1$—, aralkylcarbonyl-NR$_1$—, arylcarbonyl-NR$_1$—, heteroarylcarbonyl-NR$_1$—, alkylsulphonyl-NR$_1$—, aralkylsulphonyl-NR$_1$—, arylsulphonyl-NR$_1$— or $(R_1)_2N$-sulphonyl group or mono- or disubstituted by fluorine, chlorine or bromine atoms or by hydroxy, alkoxy or alkyl groups having 1 to 4 carbon atoms, and by the term "a heteroaryl group" used above is meant a 5-membered heteroaromatic ring which contains an oxygen, sulphur or nitrogen atom, a nitrogen atom and an oxygen, sulphur or nitrogen atom or two nitrogen atoms and an oxygen, sulphur or nitrogen atom or a 6-membered heteroaromatic ring which contains one, two or three nitrogen atoms and wherein additionally one or two —CH=N— groups may be replaced by a —CO—NR$_1$— group, whilst the above-mentioned heteroaromatic rings may additionally be substituted by one or two alkyl groups or by a fluorine, chlorine or bromine atom or by a hydroxy or alkoxy group.

Particularly preferred compounds of general formula I above are those wherein, with the proviso that the 5-membered heterocyclic ring does not denote a pyrrolidine, pyrroline, pyrrolinone or pyrrolidinone ring and contains at least one carbon atom, one of the groups $X_1$ to $X_5$ represents a group of the formula

A—B—C—N<,

A—B—C—CH< or

A—B—C—C≡ wherein A represents an amino group which is not directly bound to a phenyl ring of groups B or C, a straight-chained or branched $C_{1-3}$-aminoalkyl group, an amidino or guanidino group, whilst in the above-mentioned amino, aminoalkyl, amidino or guanidino groups, at one of the nitrogen atoms, one or two hydrogen atoms may be replaced by one or two $C_{1-4}$-alkyl groups or a hydrogen atom may be replaced by an alkoxycarbonyl group having a total or 2 to 5 carbon atoms, by an allyloxycarbonyl group, by a benzyloxycarbonyl group, by a phosphono, dimethylphosphoryl or diethylphosphoryl group or by an alkanoyloxymethoxy-carbonyl group wherein the alkanoyl moiety contains a total of 2 to 4 carbon atoms and the methoxy part may be substituted by a methyl group, or, if B or B and C together represent a cyclic imine with 6 ring members, A may also represent a hydrogen atom bound to the imino nitrogen or a methyl group bound to the imino nitrogen, B denotes a bond, a phenylene group which may be substituted by a fluorine, chlorine or bromine atom or by a methyl or methoxy group, a pyridinylene, pyrimidinylene, pyrazinylene or pyridazinylene group, a $C_{3-5}$-cycloalkylene group, a piperidinylene or 2-oxo-piperidinylene group and C denotes a phenylene group which may be substituted by a fluorine, chlorine or bromine atom or by a methyl, methoxy, methylsulphenyl, methylsulphinyl or methylsulphonyl group, an indanylene or 1,2,3,4-tetrahydronaphthylene group wherein the saturated ring in each case is bound to the group A and the aromatic ring is bound to the atom of the particular group $X_1$ to $X_5$ located in the ring, an optionally methyl-substituted pyridinylene, pyrimidinylene, pyrazinylene or pyridazinylene group or a cyclohexylene group wherein one or two CH units may each be replaced by a nitrogen atom, a second of the groups $X_1$ to $X_5$ denotes a group of the formula

F—E—D—N<,

F—E—D—CH< or

F—E—D—C≡ wherein D represents an alkylene or alkenylene group optionally substituted by a hydroxy, methoxy, amino, dimethylamino, dibenzylamino or carboxy group, or by an alkoxycarbonyl group having a total of 2 to 4 carbon atoms or by an alkoxycarbonylamino group having a total of 2 to 5 carbon atoms, in which the alkylene group contains 1 to 3 carbon atoms and the alkenylene group contains 2 or 3 carbon atoms, a phenylene group which may be substituted by a fluorine, chlorine or bromine atom or by a methyl, hydroxy, methoxy, methylsulphenyl, methylsulphinyl, methylsulphonyl, nitro, amino, acetamino, benzoylamino, methanesulphonylamino, carboxymethoxy or methoxycarbonylmethoxy group, a pyridinylene, pyrimidinylene, pyrazinylene or pyridazinylene group wherein a —CH=N— group may be replaced by a —CO—NH— group, wherein the nitrogen instead of being bound to the hydrogen atom may also be bound to the group E, provided that it is not a bond and is not bound to the group D via a heteroatom, or the nitrogen may be bound to the atom of the particular group $X_1$ to $X_5$ which is situated in the ring, provided that this is a carbon atom, a cyclohexylene group wherein a CH unit may be replaced by a nitrogen atom, or a $C_{1-2}$-alkylene group linked via the group $W_1$ to the atom of the particular group $X_1$ to $X_5$ located in the ring, provided that this is a carbon atom, wherein $W_1$ denotes an imino group or a sulphur atom, E denotes a bond, a straight-chained or branched $C_{1-4}$-alkylene group or a $C_{2-4}$-alkenylene group, each of which may be substituted by a carboxymethyl or methoxycarbonylmethyl group, or a $C_{1-2}$-alkylene group linked via the group $W_2$ to the group D, wherein $W_2$ denotes an oxygen or sulphur atom, a sulphinyl, sulphonyl, imino, methylimino or acetylimino group or an aminocarbonyl group bound to the group D via the carbonyl group, whilst E cannot be bound to a heteroatom of group D, and F represents a carbonyl group which is not bound to a heteroatom of group D but which may be substituted by a hydroxy group, by a $C_{1-4}$-alkoxy group optionally substituted in the 1-, 2- or 3-position by a cyclohexyl or phenyl group, by a $C_{5-8}$-cycloalkoxy group, by an alkanoyloxymethoxy group having a total of 2 to 6 carbon atoms in the alkanoyl moiety, by a benzoyloxymethoxy group, by an alkoxycarbonyloxymethoxy group having 1 to 3 carbon atoms in the alkoxy moiety or by a cyclohexyloxycarbonyloxymethoxy group wherein the methoxy moiety may be substituted by a methyl group, or F may represent a sulpho, phosphono, O-methyl-phosphono, O-ethyl-phosphono or tetrazol-5-yl group, whilst if A denotes an amino group, the shortest distance between this group and the group F is at least 10 bonds, a third of the groups $X_1$ to $X_5$ denotes an N-atom, an imino, methylimino, ethylimino, phenylimino, benzylimino or 2-phenylethylimino, $R_2C\equiv$ or $(R_2)_2C<$ group, wherein $R_2$ denotes a nitrogen atom, a $C_{1-7}$-alkyl group, a benzyl, phenylethyl, phenyl, pyridyl, carboxy, aminocarbonyl or alkoxycarbonyl group having a total of 2 to 4 carbon atoms, a fourth of the groups $X_1$ to $X_5$ denotes an oxygen, sulphur or nitrogen atom, an $R_2C\equiv$ group or a carbonyl group, provided that this is not located between two nitrogen atoms, a fifth of the groups $X_1$ to $X_5$ denotes a nitrogen atom, an $R_2C\equiv$ or $(R_2)_2C<$ group, wherein $R_2$ is defined as hereinbefore, or two adjacent groups of groups $X_1$ to $X_5$ together denote an o-phenylene group, but particularly those compounds of general formula I wherein, with the proviso that the 5-membered heterocyclic ring cannot denote a pyrrolidine, pyrroline, pyrrolinone or pyrrolidinone ring and contains at least one carbon atom, one of the groups $X_1$ to $X_5$ denotes a group of the formula A—B—C—N< or

A—B—C—C≡ wherein A represents an amidino group optionally substituted at one of the nitrogen atoms by an alkoxycarbonyl group having a total of 2 or 3 carbon atoms, B represents a bond or a phenylene group and C represents a phenylene or pyridazinylene group, a second of the groups $X_1$ to $X_5$ denotes a group of the formula F—E—D—N< or

F—E—D—C≡ wherein D represents an ethylene group optionally substituted by a hydroxy, amino, dibenzylamino or tert.-butoxycarbonylamino group or D may represent a phenylene group or a methylenethio group wherein the sulphur atom is bound to a carbon atom of the ring, E denotes a bond or an ethylene group and F denotes a carbonyl group which is substituted by a hydroxy or $C_{1-2}$-alkoxy group, a third of the groups $X_1$ to $X_5$ denotes an N-atom, an imino, methylimino or methine group, a fourth of the groups $X_1$ to $X_5$ denotes an oxygen, sulphur or nitrogen atom, a fifth of the groups $X_1$ to $X_5$ denotes a hydrogen atom, a methine, carboxymethine, methoxycarbonylmethine or ethoxycarbonylmethine group or two adjacent groups of groups $X_1$ to $X_5$ together denote an o-phenylene group, the tautomers thereof, the stereoisomers thereof including the mixtures and salts thereof, more particularly the physiologically acceptable salts thereof with inorganic or organic acids or bases.

The new compounds may, for example, be prepared by the following methods:

a) in order to prepare compounds of general formula I wherein F denotes a carboxyl group:

Converting a compound of general formula

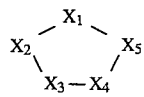   (II)

wherein $X_1$ to $X_5$ are as hereinbefore defined, with the proviso that one of the groups $X_1$ to $X_5$ denotes a group of the formula

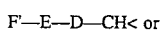

wherein E and D are as hereinbefore defined and F' denotes a group which may be converted into a carboxyl group by hydrolysis, treatment with acids, thermolysis or hydrogenolysis) into a compound of general formula I wherein F denotes a carboxyl group.

For example, functional derivatives of the carboxyl group such as unsubstituted or substituted amides, esters, thioesters, trimethylsilylesters, orthoesters, iminoesters, amidines or anhydrides, or a nitrile group may be converted by hydrolysis into a carboxyl group.

Esters with tertiary alcohols, e.g. tert.butylesters, may be converted by treatment with an acid or thermolysis into a carboxyl group and esters with aralkanols, e.g. benzylesters, may be converted by hydrogenolysis into a carboxyl group.

The hydrolysis is appropriately carried out either in the presence of an acid such as hydrochloric acid, sulphuric acid, phosphoric acid, trichloroacetic acid or trifluoroacetic acid, in the presence of a base such as lithium hydroxide, sodium hydroxide or potassium hydroxide, in a suitable solvent such as water, water/methanol, water/ethanol, water/isopropanol, methanol, ethanol or water/dioxane, at temperatures between −10° C. and 120° C., e.g. at temperatures between ambient temperature and the boiling temperature of the reaction mixture. When treating with an organic acid such as trichloroacetic acid or trifluoroacetic acid, any alcoholic hydroxy groups present may simultaneously be converted into a corresponding acyloxy group such as the trifluoroacetoxy group.

If F' in a compound of formula II represents a cyano or aminocarbonyl group, these groups may also be converted into a carboxyl group with a nitrite, e.g. sodium nitrite, in the presence of an acid such as sulphuric acid, which may appropriately be used as the solvent at the same time, at temperatures between 0° and 50° C.

If F' in a compound of formula II represents, for example, a tert.butyloxycarbonyl group, the tert.butyl group may also be cleaved by treating with an acid such as trifluoroacetic acid, formic acid, p-toluenesulphonic acid, sulphuric acid, phosphoric acid or polyphosphoric acid, optionally in an inert solvent such as methylene chloride, chloroform, benzene, toluene, tetrahydrofuran or dioxane, preferably at temperatures between −10° C. and 120° C., e.g. at temperatures between 0° and 60° C., or thermally, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40° C. and 100° C.

If F' in a compound of formula II represents, for example, a benzyloxycarbonyl group, the benzyl group may also be hydrogenolytically cleaved in the presence of a hydrogenation catalyst such as palladium/charcoal, in a suitable solvent such as methanol, ethanol, ethanol/water, glacial acetic acid, ethyl acetate, dioxane or dimethylformamide, preferably at temperatures between 0° and 50° C., e.g. at ambient temperature, under a hydrogen pressure of 1 to 5 bar. During hydrogenolysis, other groups may also be reduced at the same time, e.g. a nitro group may be reduced to an amino group or a benzyloxy group to a hydroxy group.

b) In order to prepare compounds of general formula I wherein A represents an optionally alkyl-substituted $H_2N$—C(=NH)— group:

Reacting a compound of general formula

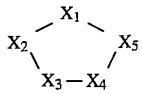   (III)

optionally formed in the reaction mixture, wherein $X_1$ to $X_5$ are as hereinbefore defined, with the proviso that one of the groups $X_1$ to $X_5$ denotes a group of the formula

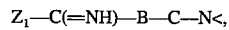

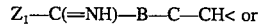

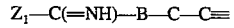

wherein B and C are as hereinbefore defined and $Z_1$ represents an alkoxy or aralkoxy group such as the methoxy, ethoxy, n-propoxy, isopropoxy or benzyloxy group or an alkylthio or aralkylthio group such as the methylthio, ethylthio, n-propylthio or benzylthio group, or an amino group, with an amine of general formula

   (IV)

wherein the groups $R_3$, which may be identical to or different from each other, denote hydrogen atoms or $C_{1-3}$- alkyl groups, or with the acid addition salts thereof.

The reaction is expediently carried out in a solvent such as methanol, ethanol, n-propanol, water, methanol/water, tetrahydrofuran or dioxane at temperatures between 0° and 150° C., preferably at temperatures between 20° and 120° C., with a corresponding free amine or with a corresponding acid addition salt such as, for example, the corresponding ammonium carbonates, acetates or chlorides.

A compound of general formula III may be obtained, for example, by reacting a corresponding nitrile with a suitable alcohol such as methanol, ethanol, n-propanol, isopropanol or benzyl alcohol in the presence of an acid such as hydrochloric acid or by reacting a corresponding amide with a trialkyloxonium salt such as triethyloxonium-tetrafluoroborate, in a solvent such as methylene chloride, tetrahydrofuran or dioxane, at temperatures between 0° and 50° C., but preferably at 20° C., or by reacting a corresponding nitrile with hydrogen sulphide, appropriately in a solvent such as pyridine or dimethylformamide and in the presence of a base such as triethylamine with subsequent alkylation of the resulting thioamide with a suitable alkyl or aralkyl halide or by reacting a corresponding nitrile with an alkoxide such as sodium methoxide in a solvent such as dioxane or tetrahydrofuran, but preferably in the alcohol in question.

c) In order to prepare compounds of general formula I wherein at least one of the groups B, C, D or E contains a sulphinyl or sulphonyl group:

Oxidising a compound of general formula

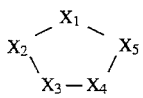 (V)

wherein $X_1$ to $X_5$ are as hereinbefore defined, with the proviso that at least one of the groups $X_1$ to $X_5$ contains a sulphenyl or sulphinyl group.

The oxidation is preferably carried out in a solvent or mixture of solvents, e.g. in water, water/pyridine, acetone, methylene chloride, glacial acetic acid, glacial acetic acid/acetic anhydride, dilute sulphuric acid or trifluoroacetic acid, at temperatures between −80° and 100° C., depending on the oxidising agent used.

In order to prepare a corresponding S-oxide compound of general formula I oxidation is appropriately carried out with one equivalent of the oxidising agent used, e.g. with hydrogen peroxide in glacial acetic acid, trifluoroacetic acid or formic acid at 0° to 20° C. or in acetone at 0° to 60° C., with a peracid such as performic acid in glacial acetic acid or trifluoroacetic acid at 0° to 50° C. or with m-chloroperbenzoic acid in methylene chloride or chloroform at −20° to 60° C., with sodium metaperiodate in aqueous methanol or ethanol at −15° to 25° C., with bromine in glacial acetic acid or aqueous acetic acid, optionally in the presence of a weak base such as sodium acetate, with N-bromosuccinimide in ethanol, with tert.butyl-hypochlorite in methanol at −80° to −30° C., with iodobenzodichloride in aqueous pyridine at 0° to 50° C., with nitric acid in glacial acetic acid at 0° to 20° C., with chromic acid in glacial acetic acid or in acetone at 0° to 20° C. and with sulphurylchloride in methylene chloride at −70° C. and the resulting thioether-chlorine complex is conveniently hydrolysed with aqueous ethanol.

In order to prepare an S,S-dioxide compound of general formula I, oxidation is expediently carried out starting from a corresponding alkylsulphynyl compound, with one or more equivalents of the oxidising agent used, or starting from a corresponding alkylsulphenyl compound with two or more equivalents of the oxidising agent used, e.g. with hydrogen peroxide in glacial acetic acid/acetic anhydride, trifluoroacetic acid or in formic acid at 20° to 100° C. or in acetone at 0° to 60° C., with a peracid such as performic acid or m-chloroperbenzoic acid in glacial acetic acid, trifluoroacetic acid, methylene chloride or chloroform at temperatures between 0° and 60° C., with nitric acid in glacial acetic acid at 0° to 20° C., with chromic acid or potassium permanganate in glacial acetic acid, water/sulphuric acid or in acetone at 0° to 20° C.

d) In order to prepare compounds of general formula I wherein A represents an amino, aminoalkyl, amidino or guanidino group substituted by an alkoxycarbonyl group having a total of 2 to 5 carbon atoms or by an aralkoxycarbonyl group:

Reacting a compound of general formula

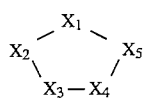 (VI)

wherein $X_1$ to $X_5$ are as hereinbefore defined, with the proviso that one of the groups $X_1$ to $X_5$ represents a group of formula

A'—B—C—N<,

A'—B—C—CH< or

A'—B—C—C≡ wherein B and C are as hereinbefore defined and A' represents an amino, aminoalkyl, $H_2N$—C(=NH)— or $H_2N$—C(=NH)—NH— group, with a compound of general formula $Z_2$—COOR$_4$ (VII)

wherein $R_4$ represents a $C_{1-4}$-alkyl group or an aralkyl group and $Z_2$ represents a nucleophilic leaving group such as a halogen atom, e.g. a chlorine or bromine atom.

The reaction is conveniently carried out in a solvent such as tetrahydrofuran, methylene chloride, chloroform or dimethylformamide, expediently in the presence of a base such as sodium carbonate, potassium carbonate or sodium hydroxide solution or in the presence of a tertiary organic base such as triethylamine, N-ethyl-diisopropylamine, N-methyl-morpholine or pyridine, which may simultaneously serve as solvent, at temperatures between −30° and 100° C., but preferably at temperatures between −10° and 80° C.

e) In order to prepare compounds of general formula I wherein F represents a carbonyl group substituted by a $C_{1-6}$-alkoxy group, wherein a $C_{1-3}$-alkoxy group may be substituted in the 1-, 2- or 3-position by an aryl or heteroaryl group or in the 2- or 3-position by a pyrrolidin-2-on-1-yl, morpholino, thiomorpholino or 1-oxido-thiomorpholino group:

Reacting a compound of general formula

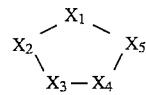 (VIII)

wherein $X_1$ to $X_5$ are as hereinbefore defined, with the proviso that one of the groups $X_1$ to $X_5$ denotes a group of the formula

F"—E—D—N<,

F"—E—D—CH< or

F"—E—D—C≡ wherein E and D are as hereinbefore defined and F" denotes a carboxy or alkoxycarbonyl group, with an alcohol of general formula

HO—R$_5$ (IX)

wherein R$_5$ represents a C$_{1-6}$-alkyl group which may be substituted in the 1-, 2- or 3-position by an aryl or heteroaryl group or in the 2- or 3-position by a pyrrolidin-2-on-1-yl, morpholino, thiomorpholino or 1-oxido-thiomorpholino group.

The reaction is conveniently carried out in a solvent or mixture of solvents such as methylene chloride, dimethylformamide, dimethylsulphoxide, benzene, chlorobenzene, tetrahydrofuran, benzene/tetrahydrofuran or dioxane, optionally in the presence of an acid such as hydrochloric acid or in the presence of a dehydrating agent, e.g. in the presence of isobutylchloroformate, thionylchloride, trimethylchlorosilane, hydrochloric acid, sulphuric acid, methanesulphonic acid, p-toluenesulphonic acid, phosphorus trichloride, phosphorus pentoxide, N,N'-dicyclohexylcarbodiimide, optionally in the presence of 4-dimethylamino-pyridine, N,N'-dicyclohexylcarbodiimide/N-hydroxysuccinimide or 1-hydroxy-benzotriazole, N,N'-carbonyldiimidazole or N,N'-thionyldiimidazole or triphenylphosphine/carbon tetrachloride, conveniently at temperatures between 0° and 150° C., preferably at temperatures between 0° and 50° C.

The reaction of a corresponding alkoxy compound with an alcohol of general formula IX is preferably carried out in a corresponding alcohol as solvent, optionally in the presence of a further solvent such as methylene chloride or ether, preferably in the presence of an acid such as hydrochloric acid at temperatures between 0° and 100° C., preferably at temperatures between 20° and 80° C.

f) In order to prepare compounds of general formula I wherein A represents an aminoalkyl group:
Reducing a compound of general formula

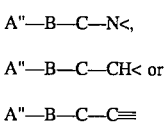

(X)

wherein X$_1$ to X$_5$ are as hereinbefore defined, with the proviso that one of the groups X$_1$ to X$_5$ denotes a group of formula

A"—B—C—N<,

A"—B—C—CH< or

A"—B—C—C≡ wherein B and C are as hereinbefore defined and A" denotes a cyano group or a cyanoalkyl group.

The reduction is preferably carried out in a suitable solvent such as methanol, methanol/water, methanol/water/ammonia, ethanol, ether, tetrahydrofuran,dioxane or dimethylformamide in the presence of catalytically activated hydrogen, e.g. hydrogen in the presence of Raney nickel, platinum or palladium/charcoal, or in the presence of a metal hydride such as sodium borohydride, lithium borohydride or lithium aluminium hydride at temperatures between 0° and 100° C., preferably at temperatures between 20° and 80° C.

g) In order to prepare compounds of general formula I wherein one of the groups X$_1$ to X$_5$ denotes an A—B—C—N< or F—E—D—N< group:
Reacting a compound of general formula

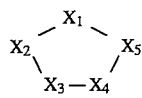

(XI)

wherein X$_1$ to X$_5$ are as hereinbefore defined, with the proviso that one of the groups X$_1$ to X$_5$ denotes an imino group, with a compound of general formula

Z$_3$—R$_6$ (XII)

wherein R$_6$ denotes a group of formula

A—B—C— or

F—E—D wherein A to F are as hereinbefore defined and Z$_3$ denotes a nucleophilic leaving group such as a halogen atom or a sulphonic acid ester group, e.g. a chlorine, bromine or iodine atom or a methanesulphonyloxy or p-toluenesulphonyloxy group.

The alkylation is conveniently carried out in a solvent or mixture of solvents such as methylene chloride, dimethylformamide, dimethylsulphoxide, benzene, chlorobenzene, tetrahydrofuran, benzene/tetrahydrofuran or dioxane, preferably in the presence of an acid binding agent, e.g. an alkoxide such as potassium tert.butoxide, an alkali metal hydroxide such as sodium or potassium hydroxide, an alkali metal carbonate such as potassium carbonate, an alkali metal amide such as sodium amide or an alkali metal hydride such as sodium hydride or a tertiary organic base such as ethyl diisopropylamine expediently at temperatures between 0° and 150° C., preferably at temperatures between 0° and 50° C.

h) In order to prepare compounds of general formula I wherein one of the groups X$_1$ to X$_5$ denotes an A—B—C—N< or F—E—D—N< group, another represents an A—B—C—C or F—E—D—C group and the remaining groups X$_1$ to X$_5$ denote nitrogen atoms:
Reacting a compound of general formula

R'—N$_2^{(+)}$X (XIII)

optionally formed in the reaction mixture with a compound of general formula

R"—CH=N—NH—Z$_4$ (XIV)

wherein the group R' denotes one said A—B—C— or F—E—D— group, the group C or the group D denoting an aryl or heteroaryl group bound to the 5-membered ring via a carbon atom, and the group R" corresponds to the other said A—B—C— or F—E—D group, and X denotes the anion of an inorganic acid such as the chloride, bromide or iodide anion.

The reaction is preferably carried out in an aqueous solvent such as methanol/water, ethanol/water or tetrahydrofuran/water in the presence of a base such as pyridine at lower temperatures, e.g. at temperatures between −20° and −10° C.

i) In order to prepare thiazoles of general formula I:
Reacting a compound of general formula

R'—CO—CH$_2$—Z$_5$ (XV)

with a compound of general formula

R''—CS—NH$_2$ (XVI)

wherein one of the groups R' or R'' denotes an A—B—C— group and the other group R' or R'' denotes an F—E—D— group and X$_5$ denotes a nucleophilic leaving group such as a chlorine, bromine or iodine atom.

The reaction is conveniently carried out in a solvent such as methanol, ethanol or isopropanol at elevated temperatures, e.g. at the boiling temperature of the solvent used.

j) In order to prepare thiazole derivatives of general formula I:

Cyclising a compound of general formula

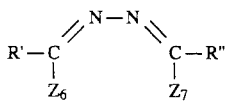
(XVII)

optionally formed in the reaction mixture, wherein Z$_6$ and Z$_7$, which may be identical to or different from each other, denote hydroxy, alkoxy, mercapto, alkylmercapto or amino groups, one of the groups R' or R'' denotes an A—B—C— group and the other group R' or R'' denotes an F—E—D— group.

The reaction is conveniently carried out in a solvent such as tetrahydrofuran, dioxane or pyridine at temperatures up to the boiling temperature of the solvent used, e.g. at temperatures between 50° and 80° C.

k) In order to prepare compounds of general formula I wherein A and B or A, B and C together denote an N-amidino cyclic imino group having 4 to 7 ring members:

Reacting a compound of general formula

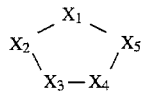
(XVIII)

wherein X$_1$ to X$_5$ are as hereinbefore defined with the proviso that B or B and C together denote a cyclic imino group having 4 to 7 ring members) with an S-alkyl-isothiourea.

The reaction is conveniently carried out in a solvent such as dimethylformamide and preferably in the presence of a base such as sodium carbonate at elevated temperatures, e.g. at temperatures between 80° and 120° C.

l) In order to prepare compounds of general formula I wherein X$_1$ to X$_5$ are as hereinbefore defined, with the proviso that one of the groups X$_1$ to X$_5$ denotes a group of formula

A—B—C—C≡, a second of groups X$_1$ to X$_5$ denotes a group of formula

F—E—D—C≡, a third of groups X to X$_5$ denotes an oxygen atom and a fourth and a fifth of groups X$_1$ to X$_5$ denotes an R$_2$C≡ group:

Dehydrating a compound of general formula

A—B—C—CO—CHR$_2$—CHR$_2$—CO—D—E—F (XIX)

wherein A to F and R$_2$ are as hereinbefore defined.

The reaction is conveniently carried out in a solvent such as methylene chloride, chloroform, benzene, toluene, xylene or chlorobenzene in the presence of a dehydrating agent such as phosphorus pentoxide, acetic anhydride, trifluoroacetic anhydride, polyphosphoric acid, sulphuric acid or phosphorus oxychloride at temperatures between 20° and 150° C., preferably at temperatures between 60° and 120° C. The reaction may also be carried out without a solvent.

m) In order to prepare compounds of general formula I wherein A denotes a guanidino group:

Reacting a compound of general formula

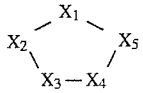
(XX)

wherein X$_1$ to X$_5$ are as hereinbefore defined, with the proviso that A denotes an amino group, with cyanamide or an acid addition salt thereof.

The reaction is conveniently carried out in a solvent such as dioxane, dioxane/water or tetrahydrofuran, preferably at temperatures between 60° and 120° C. e.g. at the boiling temperature of the reaction mixture.

n) In order to prepare compounds of general formula I wherein A denotes an amino or aminoalkyl group:

Reacting a compound of general formula

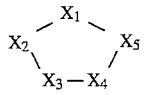
(XXI)

wherein X$_1$ to X$_5$ are as hereinbefore defined with the proviso that one of the groups X$_1$ to X$_5$ contains an H$_2$N—CO—T—B—C——group, wherein B and C are as hereinbefore defined and T denotes a bond or a C$_{1-5}$-alkylene group, with a phenyliodo(III) compound of general formula

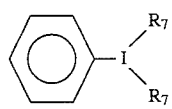
(XXII)

wherein R$_7$ denotes the acyl group of an organic carboxylic acid such as the acetoxy or trifluoroacetoxy group.

The reaction is preferably carried out in an aqueous solvent such as water or water/acetonitrile at temperatures between 0° and 50° C., but preferably at ambient temperature.

o) In order to prepare compounds of general formula I wherein A denotes an aminoalkyl group wherein the amino group is not bound to a quaternary carbon atom, or denotes an amino group which is bound to a CH or CH$_2$ group of the group B or C:

Reducing a compound of general formula

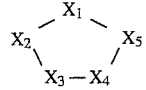
(XXIII)

wherein X$_1$ to X$_5$ are as hereinbefore defined, with the proviso that one of the groups X$_1$ to X$_5$ contains a group of the formula

A'''—B—C— wherein B and C are as hereinbefore defined and A''' contains an N-hydroxy-imino group.

The reduction is preferably carried out in a suitable solvent such as methanol, methanol/water, methanol/water/ammonia, ethanol, ether, tetrahydrofuran, dioxane or dimethylformamide, optionally with the addition of an acid such as hydrochloric acid in the presence of catalytically activated hydrogen, e.g. hydrogen in the presence of Raney nickel, platinum or palladium/charcoal, at temperatures between 0° and 100° C., preferably at temperatures between 20° and 80° C.

p) In order to prepare compounds of general formula I wherein at least one of the groups $X_1$ to $X_5$ contain an amino group substituted by one or two alkyl or aralkyl groups or an imino group substituted by an alkyl group:

Reacting a compound of general formula

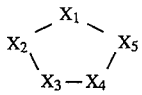

(XXIV)

wherein $X_1$ to $X_5$ are as hereinbefore defined, with the proviso that one of the groups $X_1$ to $X_5$ contains an amino, alkylamino or imino group, with a compound of general formula $$Z_8\text{—}(R_8\text{—}C\text{—}R_9)\text{—}Z_9 \quad\quad (XXV)$$

wherein $R_8$ and $R_9$, which may be identical to or different from each other, denote hydrogen atoms, alkyl, aralkyl or aryl groups, one of the groups $Z_8$ or $Z_9$ denotes a nucleophilic leaving group such as a halogen atom, e.g. a chlorine, bromine or iodine atom, or a sulphonic acid ester group, e.g. a methanesulphonyloxy or p-toluenesulphonyloxy group, and the other group $Z_8$ or $Z_9$ denotes a hydrogen atom or an alkyl group or $Z_8$ and $Z_9$ together denote an oxygen atom.

The alkylation with a compound of formula XXV wherein $Z_8$ or $Z_9$ denotes a nucleophilic leaving group is conveniently carried out in a solvent such as methylene chloride, tetrahydrofuran, dioxane, dimethylsulphoxide or dimethylformamide, optionally in the presence of a base such as sodium carbonate, potassium carbonate or sodium hydroxide solution or in the presence of a tertiary organic base such as N-ethyl-diisopropylamine or N-methyl-morpholine, which may simultaneously be used as solvent, at temperatures between –30° and 100° C., but preferably at temperatures between –10° and 80° C.

The alkylation with a carbonyl compound of general formula XXV is preferably carried in the presence of a complex metal hydride such as sodium borohydride, lithium borohydride or sodium cyanoborohydride in a solvent such as water, methanol, ethanol or methanol/water, expediently at a pH-value of 6 to 7 and at ambient temperature or in the presence of a hydrogenation catalyst, e.g. with hydrogen in the presence of palladium/charcoal, under a hydrogen pressure of 5 bar.

q) In order to prepare compounds of general formula I wherein A denotes an amino, aminoalkyl, amidino or guanidino group substituted by a dialkylphosphoryl group having 1 to 3 carbon atoms in the alkyl moiety:

Reacting a compound of general formula

(XXVI)

wherein $X_1$ to $X_5$ are as hereinbefore defined, with the proviso that one of the groups $X_1$ to $X_5$ denotes a group of formula

A'—B—C—N<,

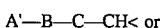

A'—B—C—CH< or

A'—B—C—C≡ wherein B and C are as hereinbefore defined and A' denotes an amino, aminoalkyl, amidino or guanidino group, with a compound of general formula $$Z_{10}\text{—}PO(OR_{10})_2 \quad\quad (XXVII)$$

wherein $R_{10}$ denotes a $C_{1-3}$-alkyl group and $Z_{10}$ denotes a nucleophilic leaving group such as a cyano group or a chlorine or bromine atom.

The reaction is expediently carried out in a solvent such as dimethylformamide at temperatures between 0° and 100° C., preferably at temperatures between 15° and 50° C. In the reactions described hereinbefore, any reactive groups present such as hydroxy, carboxy, amino, alkylamino or imino groups may optionally be protected during the reaction by means of conventional protecting groups which are cleaved again after the reaction.

For example, the protective group for a hydroxy group may be a trimethylsilyl, acetyl, benzoyl, tert.butyl, trityl, benzyl or tetrahydropyranyl group, the protecting group for a carboxyl group may be a trimethylsilyl, methyl, ethyl, tert.butyl, benzyl or tetrahydropyranyl group and the protecting group for an amino, alkylamino or imino group may be an acetyl, benzoyl, ethoxycarbonyl, tert.-butoxycarbonyl, benzyloxycarbonyl, benzyl, methoxybenzyl or 2,4-dimethoxybenzyl group and for the amino group a phthalyl group may also be considered.

The optional subsequent cleaving of a protecting group may, for example, be carried out hydrolytically in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or by ether cleaving, e.g. in the presence of iodotrimethylsilane, at temperatures between 0° and 100° C., preferably at temperatures between 10° and 50° C.

However, a benzyl, methoxybenzyl or benzyloxy-carbonyl group may be cleaved hydrogenolytically, for example, using hydrogen in the presence of a catalyst such as palladium/charcoal in a solvent such as methanol, ethanol, ethyl acetate or glacial acetic acid, optionally with the addition of an acid such as hydrochloric acid at temperatures between 0° and 50° C., but preferably at ambient temperature, under a hydrogen pressure of 1 to 7 bar, preferably 3 to 5 bar.

A methoxybenzyl group may also be cleaved in the presence of an oxidising agent such as cerium(IV)-ammonium nitrite in a solvent such as methylene chloride, acetonitrile or acetonitrile/water at temperatures between 0° and 50° C., but preferably at ambient temperature.

However, a 2,4-dimethoxybenzyl group is preferably cleaved in trifluoroacetic acid in the presence of anisole.

A tert.butyl or tert.butyloxycarbonyl group is preferably cleaved by treating with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20° and 50° C.

If according to the invention a compound of general formula I is obtained which contains a carboxy group, this may be converted by esterification into a corresponding ester compound.

The subsequent esterification is conveniently carried out in a suitable solvent, e.g. in a corresponding alcohol such as methanol, ethanol or isopropanol, or in methylene chloride, tetrahydrofuran, dioxane, pyridine, toluene or dimethylsulphoxide, in the presence of an acid activating and/or dehydrating agent such as hydrogen chloride, conc. sulphuric acid, thionyl chloride, ethyl chloroformate, carbonyldiimidazole or N,N'-dicyclohexyl-carbodiimide or the isourea esters thereof, optionally in the presence of a reaction accelerator such as copper chloride, by transesterification, e.g. with a corresponding carbonic acid diester, or by reacting with a corresponding halide, preferably in the presence of a base such as potassium carbonate and optionally in the presence of a reaction accelerator such as potassium iodide at temperatures between 0° and 100° C., but preferably at temperatures between 20° C. and the boiling temperature of the solvent in question.

Furthermore, the compounds of general formula I obtained may be resolved into their enantiomers and/or diastereomers as mentioned hereinbefore. Thus, for example, cis/trans mixtures may be resolved into their cis and trans isomers, and compounds having at least one optically active carbon atom may be resolved into their enantiomers.

Thus, for example, the cis/trans mixtures obtained may be resolved by chromatography into the cis and trans isomers thereof and the compounds of general formula I which occur in racemate form may be separated by methods known per se (cf. Allinger N. L. and Eliel E. L in "Topics in Stereochemistry", Vol 6, Wiley Interscience, 1971) into their optical antipodes, and compounds of general formula I having at least 2 asymmetric carbon atoms may be separated on the basis of their physical-chemical differences using known methods e.g. by chromatography and/or fractional crystallization, into the diastereomers thereof which, if they occur in racemic form, may subsequently be separated into the enantiomers as mentioned above.

The separation of enantiomers is preferably effected by column separation on chiral phases or by recrystallisation from an optically active solvent or by reacting with an optically active substance, especially an acid or an activated derivative thereof or an alcohol, which forms salts or derivatives such as for example, esters or amides with the racemic compound, and separation of the diastereomeric salt mixture or derivative thus obtained, e.g. on the basis of their different solubilities, whilst the free antipodes may be released from the pure diastereomeric salts or derivatives by the action of suitable agents. Particularly common, optically active acids include, for example, the D- and L-forms of tartaric acid or dibenzoyltartaric acid, di-o-tolyl tartaric acid, malic acid, mandelic acid, camphorsulphonic acid, glutamic acid, aspartic acid or quinic acid. The optically active alcohol may be (+)- or (−)-menthol, for example, and the optically active acyl group in amides may be, for example, (+)- or (−)-menthyloxycarbonyl.

Moreover, the compounds of formula I obtained may be converted into the salts thereof, particularly for pharmaceutical use into the physiologically acceptable salts thereof with inorganic or organic acids. Examples of suitable acids include hydrochloric acid, hydrobromic acid, sulphuric acid, phosphoric acid, acetic acid, fumaric acid, succinic acid, lactic acid, citric acid, tartaric acid or maleic acid.

In addition, the new compounds of formula I thus obtained, if they contain a carboxyl group, may subsequently, if desired, be converted into the addition salts thereof with inorganic or organic bases, more particularly, for pharmaceutical use, into the physiologically acceptable addition salts thereof. Examples of suitable bases include sodium hydroxide, potassium hydroxide, ammonia, cyclohexylamine, ethanolamine, diethanolamine and triethanolamine.

The compounds used as starting materials are known from the literature in some cases or may be obtained by methods known from the literature, as described in Examples I to XII.

As already mentioned, the new 5-membered heterocylic compounds of general formula I and the addition salts thereof, particularly the physiologically acceptable addition salts thereof with inorganic or organic acids or bases, have valuable properties. Thus, the new compounds of general formula I, wherein A contains an amino, aminoalkyl, amidino or guanidino group optionally substituted at the nitrogen or a group which may optionally be converted in vivo into an amino, amidino or guanidino group optionally substituted at the nitrogen, e.g. an amino, aminoalkyl, amidino or guanidino group substituted at the nitrogen by an alkoxycarbonyl group, or B or B and C together denote a cyclic imino group optionally alkylated at the nitrogen atom and —D—E—F contains carboxyl, sulpho, phosphono, O-alkylphosphono or 5-tetrazolyl groups or groups which can be converted in vivo into carboxyl, sulpho, phosphono, O-alkyl-phosphono or tetrazolyl groups, e.g. carbonyl groups substituted by an alkoxy group, have valuable pharmacological properties; in addition to having an inhibitory effect on inflammation and bone degradation, they have in particular, antithrombotic, antiaggregatory and tumour- or metastasis-inhibiting effects.

The compounds of general formula I wherein A denotes a cyano or cyanoalkyl group are valuable intermediate products for preparing the corresponding aminoalkyl and amidino compounds of general formula I.

By way of example, the compounds of general formula I were investigated for their biological effects as follows:

1. Fibrinogen binding to human thrombocytes

The blood obtained by puncturing an antecubital vein is anticoagulated with trisodium citrate (final concentration: 13 mM) and centrifuged for 10 minutes at 170×g. The supernatant platelet-rich plasma is poured onto a Sepharose 2B column (Pharmacia) and eluted with a solution of 90 mM common salt, 14 mM trisodium citrate, 5 mM glucose and 50 mM Tris(hydroxymethyl)aminomethane, adjusted to pH 7.4. The gel-filtered platelets (GFP) appearing before the plasma proteins are used for the binding experiments.

50 µl of a 60 mM calcium chloride solution, 50 µl of a 0.6 mM adenosine diphosphate solution, 100 µl of substance solution or solvent and 50 µl of fibrinogen solution (containing 3 µg of $^{125}$I fibrinogen) are added to 750 µl of GFP and incubated for 20 minutes at ambient temperature. The non-specific binding is determined in the presence of 3 mg/ml of cold fibrinogen.

900 µof the incubated material are carefully pipetted onto 250 µof silicon oil (AP 38: AR 20, 1:2 v/v, Wacker Chemie) in Eppendorf tubes and centrifuged for 2 minutes at 10,000× g. The aqueous supernatant and part of the oil are drawn off, the tips of the tubes are cut off together with the platelet pellet and the quantity of bound fibrinogen is determined in a gamma counter. The concentration of substance which brings about a 50% inhibition in fibrinogen binding is determined from a series of concentrations and is given as the $IC_{50}$ value.

2. Antithrombotic activity

Method

The thrombocyte aggregation is measured using the Born and Cross method (J. Physiol. 170: 397 (1964)) in platelet-rich plasma taken from healthy volunteers. To inhibit coagulation the blood is mixed with 3.14% sodium citrate in a ratio by volume of 1:10.

Collagen-induced aggregation

The pattern of the decrease in optical density of the platelet suspension is photometrically measured and recorded after the addition of the aggregation-triggering substance. The rate of aggregation is concluded from the angle of inclination of the density curve. The point on the curve where there is maximum light transmittance is used to calculate the optical density.

The amount of collagen used is as small as possible but sufficient to produce an irreversible reaction curve. Standard commercial collagen produced by Hormonchemie of Munich is used. Before the addition of the collagen the plasma is incubated for 10 minutes with the substance at 37° C.

From the measurements obtained an $EC_{50}$ is determined graphically, indicating a 50% change in the optical density in terms of the inhibition of aggregation.

The Table which follows contains the results found:

| Substance (Example No.) | Fibrinogen-binding test $IC_{50}[nM]$ | Inhibition of platelet aggregation $EC_{50}[nM]$ |
| --- | --- | --- |
| 1 | 73 | 130 |
| 1(1) | 38 | 90 |
| 1(2) | 18 | 90 |
| 1(3) | 220 | 11,000 |
| 1(4) | 44 | 290 |
| 1(6) | 25 | 90 |
| 1(7) | 210 | 580 |
| 1(8) | 460 | 4,100 |
| 1(9) | 4,200 | 8,500 |
| 1(10) | 2,000 | 9,500 |
| 1(20) | 65 | 290 |
| 1(35) | 2,400 | 6,900 |
| 1(37) | 150 | 2,400 |
| 1(39) | 39 | 3,700 |
| 1(127) | 2,500 | 14,000 |
| 1(128) | 3,500 | 9,000 |
| 1(134) | 460 | 510 |
| 2 | 510 | 2,200 |
| 2(1) | — | 180 |
| 2(2) | 340 | 350 |
| 2(3) | 140 | 1,600 |
| 2(4) | 490 | 370 |
| 2(5) | 3,100 | 7,500 |
| 2(6) | 4,300 | 210 |
| 2(7) | 17,000 | 800 |
| 2(8) | 44,000 | 6,400 |
| 2(10) | — | 220 |
| 2(20) | 4,900 | 280 |
| 2(37) | 6,200 | 6,100 |
| 2(39) | 130 | 5,400 |
| 2(126) | 1,400 | 22,000 |
| 4(1) | 1,500 | — |
| 4(2) | 1,800 | — |

The compounds according to the invention are well tolerated because after intravenous administration of 30 mg/kg of the compounds of Examples 1 and 1(2) to each of three mice, no animals died.

In the light of their inhibitory effect on cell-to-cell or cell-to-matrix interactions, the new 5-membered heterocyclic compounds of general formula I and the physiologically acceptable addition salts thereof are suitable for treating or preventing diseases in which smaller or greater cell aggregates occur or in which cell-to-matrix interactions play a part, e.g. in treating or preventing venous and arterial thrombosis, cerebrovascular diseases, lung embolism, cardiac infarction, arteriosclerosis, osteoporosis and the metastasis of tumours and the treatment of genetically caused or acquired disorders of cell interactions with one another or with solid structures. They are also suitable for parallel therapy in thrombolysis with fibrinolytics or vascular interventions such as transluminal angioplasty or in the treatment of shock, psoriasis, diabetes and inflammation.

For treating or preventing the diseases mentioned above the dosage is between 0.1 µg and 20 mg/kg of body weight, preferably 1 µg to 10 mg/kg of body weight, given in up to 4 doses per day. For this purpose the compounds of formula I produced according to the invention, optionally in conjunction with other active substances such as thromboxane receptor antagonists and thromboxane synthesis inhibitors or combinations thereof, serotonin antagonists, e-receptor antagonists, alkylnitrates such as glycerol trinitrate, phospho-diesterase inhibitors, prostacyclin and the analogues thereof, fibrinolytics such as tPA, prourokinase, urokinase, streptokinase, or anticoagulants such as heparin, dermatane sulphate, activated protein C, vitamin K antagonists, hirudine, inhibitors of thrombin or other activated clotting factors, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene-glycol, propyleneglycol, stearylalcohol, carboxymethyl-cellulose or fatty substances such as hard fat or suitable mixtures thereof, into conventional galenic preparations such as plain or coated tablets, capsules, powders, suspensions, solutions, sprays or suppositories.

The Examples which follow are intended to illustrate the invention:

EXAMPLE I

Methyl 3-(4-imidazolyl)-propionate 2.3 g of methyl 3-(4-imidazolyl)-acrylate are treated in 50 ml of methanol in the presence of 0.5 g of 10% palladium/charcoal for 4 hours at ambient temperature under 5 bars of hydrogen. After the catalyst is filtered off the filtrate has been evaporated down in vacuo and the residue remaining is used as a crude product.

Yield: 2.3 g (100% of theory), $R_f$ value: 0.35 (silica gel; methylene chloride/methanol 9:1)

The following compound is obtained analogously:

(1) 3-(4-imidazolyl)-propionic acid 10 vol.-% of 1N hydrochloric acid are added and the mixture is hydrogenated for one hour at 50° C.

$R_f$ value: 0.48 (silica gel; methylene chloride/methanol/conc. ammonia=4:1:0.25) The methylester is obtained therefrom by treating with saturated methanolic hydrochloric acid.

EXAMPLE II 5-(4-Cyano-4'-biphenylyl)-tetrazole

A solution of 0.5 g of aluminium trichloride in 3 ml of tetrahydrofuran is added dropwise to a stirred suspension of 1.5 g of 4,4'-dicyanobiphenyl and 0.75 g of sodium azide in 3 ml of tetrahydrofuran and the mixture is refluxed for 16 hours. A further 0.2 g of sodium azide and 0.15 g of aluminium trichloride, dissolved in 1 ml of tetrahydrofuran, are added and the mixture is refluxed for a further 6 hours. It is made acidic with 1N hydrochloric acid and the tetrahydrofuran is distilled off in vacuo. The crude product precipitated is purified by chromatography on silica gel (eluant: methylene chloride/methanol/conc. ammonia=4:1:0.25).

Yield: 0.9 g (50% of theory), $R_f$ value: 0.28 (silica gel; methylene chloride/methanol/conc. ammonia=4:1:0.25)

EXAMPLE III 4-(2-Methoxycarbonyl-ethyl)-thiobenzoic acid amide 5 g of 4-(2-methoxycarbonyl-ethyl)-benzamide, 5 g of 2,4-bis(4-methoxy-phenyl)-1,3-dithia- 2,4-diphosphetan-2,4-disulphide and 50 ml of tetrahydrofuran are stirred for 4

EXAMPLE IV 4-(2-Methoxycarbonyl-ethyl)-benzamidine-hydrochloride

Prepared analogously to Example 2 from methyl 3-(4-cyano-phenyl)-propionate.

Melting point: 175°–178° C. $R_f$ value: 0.78 (Reversed phase plate; 5% sodium chloride solution/methanol=4:6)

EXAMPLE V

Methyl 3-(4-cyano-phenyl)-propionate 30.1 g of 3-(4-cyano-phenyl)-propionic acid are dissolved in 760 ml of methanol and 30 ml of saturated methanolic hydrochloric acid are added. The mixture is stirred for 16 hours at ambient temperature, evaporated down in vacuo, taken up in tert.butylmethylether and washed with water. The crude product remaining after evaporation of the organic phase is used again without any further purification.

Yield: 30.7 g (89% of theory), Melting point: 44°–48° C.

The following compound is obtained analogously:

(1) Methyl 3-(3-indolyl)-propionate $R_f$ value: 0.39 (silica gel; cyclohexane/ethyl acetate=3:1)

EXAMPLE VI 3-(4-Cyano-phenyl)-propionic acid 39.4 g of (4-cyano-benzyl)-malonic acid, 45 ml of pyridine and 0.8 ml of piperidine are stirred at 100° C. for 1.5 hours. After cooling, 450 ml of ice water are added. The mixture is acidified with 300 ml of 2N hydrochloric acid and extracted with ethyl acetate. The organic phase is washed with saturated saline solution and evaporated down. The residue remaining is used again without any further purification.

Yield: 30.1 g (94% of theory), $R_f$ value: 0.46 (silica gel; methylene chloride/methanol=19:1)

EXAMPLE VII (4-Cyano-benzyl)-malonic acid 63 g of triethyl (4-cyano-benzyl)-methane-tricarboxylate are dissolved in 160 ml of methanol and a mixture of 37 ml of 15N sodium hydroxide solution and 16 ml of methanol is added dropwise with stirring. The resulting mixture is refluxed for 30 minutes, mixed with ice water and extracted with ethyl acetate. The aqueous phase is acidified with semiconcentrated hydrochloric acid and extracted with ethyl acetate. The ethyl acetate phase is washed with saturated sodium chloride solution and evaporated down. The crude product remaining is further processed without any further purification.

Yield: 39.4 g (98% of theory), $R_f$ value: 0.47 (silica gel; methylene chloride/methanol=19:1)

EXAMPLE VIII

Triethyl (4-cyano-benzyl)-methane-tricarboxylate 44.9 g of triethylmethane-tricarboxylate are dissolved in 180 ml of dimethylformamide and mixed with 21.9 g of potassium tert.butoxide. The mixture is cooled to ambient temperature, 36.2 g of 4-cyano-benzylbromide are added and the mixture is stirred for 16 hours at ambient temperature. The potassium bromide formed is filtered off and the solvent is evaporated off in vacuo. The crude product remaining is used again without any further purification.

Yield: 63 g (99% of theory), $R_f$ value: 0.80 (silica gel; methylene chloride/methanol=19:1)

The following compound is obtained analogously:

(1) ethyl 7-(4-cyano-4'-biphenylyl)-6-ethoxycarbonyl-4,7-dioxoheptanoate

Prepared from ethyl (4-cyano-4'-biphenylyl)-carbonyl-acetate and 5-bromo-laevulinic acid by refluxing in acetone in the presence of potassium carbonate.

$R_f$ value: 0.42 (silica gel; ethyl acetate/cyclohexane=1:25, developed twice)

EXAMPLE IX

N-(4-Cyano-benzoyl)-N'-[4-(2-methoxycarbonyl-ethyl)-benzoyl]-hydrazine

To a suspension of 1.86 g of 4-cyano-benzhydrazide (prepared from methyl 4-cyano-benzoate and 80% hydrazine hydrate) in 25 ml of methylene chloride are added 3.1 g of N-ethyl-diisopropylamine and then a solution of 4-(2-methoxycarbonyl-ethyl)benzoylchloride (prepared from the corresponding benzonitrile via the amide and the acid) is added dropwise thereto and the resulting mixture is left to stand for 24 hours at ambient temperature. The methylene chloride phase is washed with water, 1N hydrochloric acid and water and evaporated down. The residue is digested with a little methanol and the solid product formed is filtered off.

Yield: 1.7 g (42% of theory), $R_f$ value: 0.51 (silica gel; methylene chloride/methanol=19:1)

The following compounds are obtained analogously:

(1) 1-[(4-cyano-4'-biphenylyl)-carbonyl]-thiosemicarbazide

Glacial acetic acid is used as solvent and sodium acetate as base.

Melting point: 231° C. (decomp.)

(2) N-[(4-cyano-4'-biphenylyl)-carbonyl]-N'-(2-methoxycarbonylethylcarbonyl)-hydrazine $R_f$ value: 0.78 (silica gel; methylene chloride/methanol= 17:3)

EXAMPLE X

Ethyl (4-cyano-4'-biphenylyl)-carbonyl-acetate 14.9 g of monoethyl-malonate are dissolved in 750 ml of tetrahydrofuan and at −65° to −70° C., 141 ml of a 1.6 molar solution of n-butyllithium in hexane are added. The resulting mixture is stirred for 15 minutes at −65° C. and for a further hour at 0° C., then cooled to −65° C. and a solution of 18.1 g of 4'-cyano-4-biphenylylcarbonyl chloride in 75 ml of tetrahydrofuran is added dropwise with stirring. The mixture is stirred for a further 45 minutes at −60° C., allowed to come up to 0° C. and then stirred for a further 3 hours at 0° C. The reaction mixture is stirred into an ice cold mixture of 125 ml of 1N hydrochloric acid and 300 ml of ether. The organic phase is washed with sodium bicarbonate solution and water and the aqueous phases are extracted with ether. The combined organic phases are evaporated to dryness and the residue is purified over silica gel (eluant: ethyl acetate/cyclohexane=1:2.5).

Yield: 16.1 g (69% of theory), Melting point: 89°–91° C. $R_f$ value: 0.64 (silica gel; ethyl acetate/cyclohexane=1:2.5 developed twice)

EXAMPLE XI

3-Chloro-6-(4-methoxycarbonylamidino-phenyl)-pyridazine

Prepared from 3-chloro-6-(4-amidino-phenyl)-pyridazine and methyl chloroformate analogously to Example 4.

EXAMPLE XII 3-(4-Cyano-4'-biphenylyl)-5-mercapto-1,2,4-triazole 1.2 g of 1-[(4-cyano-4'-biphenylyl)-carbonyl]-thiosemicarbazide are heated in a solution of 0.43 g of sodium carbonate in 5 ml of water over a vapour bath for 1.5 days. Ammonium chloride solution is added, the precipitate is filtered off and dried at 80° C.

Yield: 1.1 g (88% of theory), Melting point: over 275° C. $R_f$ value: 0.66 (silica gel; ethyl acetate/ethanol=50:2)

EXAMPLE 1

1-[6-(4-Amidino-phenyl-3-pyridazinyl]-4-(2-carboxy-ethyl)-imidazole

A mixture of 0.18 g of 1-[6-(4-amidino-phenyl)-3-pyridazinyl]-4-(2-methoxycarbonyl-ethyl)-imidazole, 0.087 g of lithium hydroxide-hydrate, 20 ml of tetrahydrofuran and 16 ml of water is stirred for 2 hours at ambient temperature. 1 g of ammonium chloride is added and the mixture is stirred for 30 minutes. The tetrahydrofuran is distilled off in vacuo, the precipitate formed is suction filtered, washed with water and dried.

Yield: 0.13 g (76% of theory), Melting point: over 260° C. $R_f$ value: 0.12 (silica gel; methylene chloride/methanol/ conc. ammonia=2:1:0.25)

The following compounds are obtained analogously:

(1) 1-[-6-(4-amidino phenyl)-3-pyridazinyl]-4-(2-carboxy-2-hydroxy-ethyl)-imidazole $R_f$ value: 0.09 (silica gel; methylene chloride/methanol/ conc. ammonia=2:1:0.25 )

(2) 1-[6-(4-amidino-phenyl)-3-pyridazinyl]-4-(2-amino-2-carboxy-ethyl)-imidazole-hydrochloride $R_f$ value: 0.04 (silica gel; methylene chloride/methanol/ conc. ammonia=2:1:0.25) Calculated x 0.6 HCl x 0.75 $H_2O$: C 52.80 H 4.78 N 25.36 Cl 5.51 Found 53.29 4.76 24.97 5.99

(3) 5-(4-amidino-phenyl)-2-[4-(2-carboxy-ethyl)-phenyl]-tetrazole $R_f$ value: 0.06 (silica gel; methylene chloride/methanol/ conc. ammonia=2:1:0.25) Calculated x $H_2O$: 57.62 H 5.12 N 23.72 Found: 57.57 5.17 23.41

(4) 5-(4-amidino-4'-biphenylyl)-2-(2-carboxy-ethyl)-tetrazole $R_f$ value: 0.06 (silica gel; methylene chloride/methanol/ conc. ammonia=2:1:0.25)

(5) 4-(4-amidino-phenyl)-2-[4-(2-carboxy-ethyl)-phenyl]-thiazole

The work is done with sodium hydroxide solution in methanol

Melting point: 310°–315° C. (decomp.) $R_f$ value: 0.32 (Reversed phase plate RP8; 5% sodium chloride solution/ methanol=4:6)

(6) 4-(4-amidino-phenyl)-2-[4-(2-carboxy-ethyl)-phenyl]-1-methyl-imidazole

The same procedure is used as in (5)

Melting point: over 200° C. $R_f$ value: 0.79 (Reversed phase plate RP8; 5% sodium chloride solution/methanol= 4:6) Calculated x 0.5 $H_2O$ C 67.21 H 5.92 N 15.68 Found: 67.24 6.04 15.61

(7) 4-(4-amidino-phenyl)-2-[4-(2-carboxy-ethyl)-phenyl]-imidazole

The same procedure is used as in (5)

Melting point: 310°–315° C. (decomp.) $R_f$ value: 0.75 (Reversed phase plate RP8; 5% sodium chloride solution/ methanol=4:6) Calculated: C 68.25 H 5.43 N 16.76 Found: 67.72 5.36 16.71

(8) 3-(4-amidino-phenyl)-5-[4-(2-carboxy-ethyl)-phenyl]-1,2,4-triazole

The same procedure is used as in (5)

$R_f$ value: 0.08 (silica gel; methylene chloride/methanol= 7:3)

(9) 2-(4-amidino-phenyl)-5-[4-(2-carboxy-ethyl)-phenyl]-1,3,4-oxadiazole

The same procedure is used as in (5)

$R_f$ value: 0.08 (silica gel; methylene chloride/methanol= 7.5:2.5)

(10) 2-(4-amidino-phenyl)-5-[4-(2-carboxy-ethyl)-phenyl]-1,3,4-thiadiazole $R_f$ value: 0.17 (silica gel; methylene chloride/methanol= 7:3)

(11) 1-[5-(4-amidino-phenyl)-2-pyrimidyl]-4-(2-amino-2-carboxy-ethyl)-imidazole

(12) 1-[5-(4-amidino-phenyl)-4-methyl-2-pyrimidyl]-4-(2-amino-2 -carboxy-ethyl)-imidazole

(13) 1-[5-(4-amidino-phenyl)-2-pyrazinyl]-4-(2-amino-2-carboxy-ethyl)-imidazole

(14) 1-[5-(4-amidino-phenyl)-4-methyl-2-pyrimidyl]-4-(2-carboxy-ethyl)-imidazole

(15) 1-[5-(4-amidino-phenyl)-2-pyrimidyl]-4-(2-carboxy-ethyl)-imidazole

(16) 1-(4-amidino-4'-biphenylyl)-4-(2-carboxy-ethyl)-imidazole

(17) 4-(4-amidino-4'-biphenylyl)-2-(2-carboxy-ethyl)-thiazole

(18) 5-(4-amidino-4'-biphenylyl)-2-(2-carboxy-ethyl)-oxazole

(19) 2-(4-amidino-4'-biphenylyl)-5-(2-carboxy-ethyl)-1,3,4-oxadiazole

(20) 2-(4-amidino-4'-biphenylyl)-5-(2-carboxy-ethyl)-1,3,4-thiadiazole

The work is done with sodium hydroxide $R_f$ value: 0.16 (silica gel; methylene chloride/methanol= 17:3)

(21) 2-(4-amidino-4'-biphenylyl)-4-(2-carboxy-ethyl)-thiazole

(22) 2-(4-amidino-4'-biphenylyl)-5-(2-carboxy-ethyl)-thiophene

(23) 2-(4-amidino-4'-biphenylyl)-5-(2-carboxy-ethyl)-furan

(24) 1-(4-amidino-3'-bromo-4'-biphenylyl)-4-(2-carboxy-ethyl)-imidazole

(25) 1-[6-(4-amidino-phenyl)-3-pyridazinyl]-4-(2-carboxy-ethyl)- 2-methyl-imidazole

(26) 1-[6-(4-amidino-phenyl)-3-pyridazinyl]-4-(2-carboxy-ethyl)-2-isopropyl-imidazole

(27) 1-[6-(4-amidino-phenyl)-3-pyridazinyl]-4-(2-carboxy-ethyl)-2-hexyl-imidazole

(28) 1-[6-(4-amidino-phenyl)-3-pyridazinyl]-4-(2-carboxy-ethyl)-2-(2-phenyl-ethyl)-imidazole

(29) 1-[6-(4-amidino-phenyl)-3-pyridazinyl]-4-(2-carboxy-ethyl)-2-phenyl-imidazole

(30) 1-[6-(4-amidino-phenyl)-3-pyridazinyl]-4-(2-carboxy-ethyl)-2-(3-pyridyl)-imidazole

(31) 3-(4-amidino-4'-biphenylyl)-5-(2-carboxy-ethyl)-1,2,4-triazole

(32) 1-[6-(4-amidino-phenyl)-3-pyridazinyl]-4-(3-carboxy-propyl)-imidazole

(33) 2-(4-amidino-3'-methoxy-4'-biphenylyl)-5-(2-carboxy-ethyl)-1,3,4-thiadiazole

(34) 2-(4-amidino-3'-methyl-4'-biphenylyl)-5-(2-carboxy-ethyl)-1,3,4-thiadiazole

(35) 1-[6-(4-amidino-phenyl)-3-pyridazinyl]-4-(2-carboxy-2 -dibenzylamino-ethyl)-imidazole $R_f$ value: 0.35 (silica gel; methylene chloride/methanol= 15:1)

$R_f$ value: 0.21 (silica gel; methylene chloride/methanol/conc. ammonia=2:1:0.25)

(36) 1-[6-(4-amidino-phenyl)-3-pyridazinyl]-4-(2-carboxy-2-dimethylamino-ethyl)-imidazole

(37) 1-[6-(4-amidino-phenyl)-3-pyridazinyl]-3-(2-carboxy-ethyl)-indole

Melting point: 288°–292° C. $R_f$ value: 0.03 (silica gel; methylene chloride/methanol/conc. ammonia=2:1:0.25)

(38) 4-(4-amidino-4'-biphenylyl)-2-(2-carboxy-ethyl)-5-methylthiazole

(39) 3-(4-amidino-4'-biphenylyl)-5-carboxymethylthio-1,2,4-triazole

The work is done with sodium hydroxide

Melting point: over 245° C. Calculated x 4 $H_2O$: C 48.00 H 5.44 N 16.46 Found: 47.52 5.61 16.45

(40) 4-(4-amidino-4'-biphenylyl)-2-carboxymethylamino-thiazole

(41) 2-[1-(4-amidino-phenyl)-4-piperidinyl]-4-(2-carboxy-ethyl)-thiazole

(42) 2-[4-(4-amidino-phenyl)-1-piperazinyl]-4-(2-carboxy-ethyl)-thiazole

(43) 2-[1-(5-amidino-2-pyridyl)-4-piperidinyl]-4-(2-carboxy-ethyl)-thiazole

(44) 1-[4-(5-amidino-2-pyrimidyl)-phenyl]-4-(2-carboxy-ethyl)-imidazole

(45) 1-[4-(5-amidino-2-pyrazinyl)-phenyl]-4-(2-carboxy-ethyl)-imidazole

(46) 4-[4-(1-amidino-4-piperidinyl)-phenyl]-2-(2-carboxy-ethyl)-thiazole

(47) 1-[4-(4-amidino-phenyl)-cyclohexyl]-4-(2-carboxy-ethyl)-imidazole

(48) 1-[6-(4-amidino-phenyl)-3-pyridazinyl]-3-(2,2-bis-carboxy-ethyl)-indole

(49) 2-[1-(4-amidino-phenyl)-4-piperidinyl]-5-(2-carboxy-ethyl)-1,3,4-oxadiazole

(50) 2-[1-(5-amidino-2pyridyl)-4-piperidinyl]-5-(2-carboxy-ethyl)- 1,3,4-oxadiazole

(51) 5-[1-(4-amidino-phenyl)-4-piperidinyl]-2-(2-carboxy-ethyl)-tetrazole

(52) 5-[1-(5-amidino-2-pyridyl)-4-piperidinyl]-2-(2-carboxy-ethyl)-tetrazole

(53) 2-[6-(4-amidino-phenyl)-3-pyridazinyl]-4-(2-carboxy-ethyl)-1,2,3-triazole

(54) 1-[6-(4-amidino-phenyl)-3-pyridazinyl]-4-(2-carboxy-ethyl)-1,2,3-triazole

(55) 1-[6-(4-amidino-2-methyl-phenyl)-3-pyridazinyl]-4-(2-carboxy-ethyl)-imidazole

(56) 1-[6-(4-aminomethyl-phenyl)-3-pyridazinyl]-4-(2-carboxy-ethyl)-imidazole

(57) 2-(4-amidino-phenyl)-4-[4-(2-carboxy-ethyl)-phenyl]-thiazole

(58) 2-(4-amidino-phenyl)-4-[4-(2-carboxy-ethyl)-phenyl]-1-methyl-imidazole

(59) 5-(4-amidino-phenyl)-2-[4-(2-carboxy-ethyl)-phenyl]-thiazole

(60) 2-(4-amidino-phenyl)-4-[4-(2-carboxy-ethyl)-phenyl]-imidazole

(61) 1-(4-amidino-phenyl)-3-[4-(2-carboxy-ethyl)-phenyl]-5-methyl-1,2,4-triazole

(62) 3-(4-amidino-phenyl)-5-[4-(2-carboxy-ethyl)-phenyl]-pyrazole

(63) 5-(4-amidino-phenyl)-3-[4-(2-carboxy-ethyl)-phenyl]-1-methyl-pyrazole

(64) 3-(4-amidino-phenyl)-5-[4-(2-carboxy-ethyl)-phenyl]-1-phenyl-pyrazole

(65) 1-(4-amidino-phenyl)-4-[4-(2-carboxy-ethyl)-phenyl]-2-methyl-imidazole

(66) 1-(4-amidino-phenyl)-4-[4-(2-carboxy-ethyl)-phenyl]-2-phenyl-imidazole

(67) 4-(4-amidino-phenyl)-1-[4-(2-carboxy-ethyl)-phenyl]-imidazole

(68) 1-(4-amidino-phenyl)-3-[4-(2-carboxy-ethyl)-phenyl]-2H-pyrazol-5-one

(69) 1-(4-amidino-phenyl)-3-[4-(2-carboxy-ethyl)-phenyl]-2-methyl-2H-pyrazole-5-one

(70) 3-(4-amidino-phenyl)-1-[4-(2-carboxy-ethyl)-phenyl]-2H-pyrazol-5-one

(71) 3-(4-amidino-phenyl)-1-[4-(2-carboxy-ethyl)-phenyl]-2-methyl-2H-pyrazole-5-one

(72) 1-(4-amidino-phenyl)-3-[4-(2-carboxy-ethyl)-phenyl]-1,2,4-triazole

(73) 3-(4-amidino-phenyl)-1-[4-(2-carboxy-ethyl)-phenyl]-1,2,4-triazole

(74) 4-(4-amidino-phenyl)-2-[4-(2-carboxy-ethyl)-phenyl]-oxazole

(75) 4-(4-amidino-phenyl)-2-[4-(2-carboxy-ethyl)-phenyl]-1-phenyl-imidazole

(76) 1-(4-amidino-phenyl)-3-[4-(2-carboxy-ethyl)-phenyl]-pyrazole

(77) 1-(4-amidino-phenyl)-3-[4-(2-carboxy-ethyl)-phenyl]-5-methyl-pyrazole

(78) 3-(4-amidino-phenyl)-1-[4-(2-carboxy-ethyl)-phenyl]-pyrazole

(79) 3-(4-amidino-phenyl)-1-[4-(2-carboxy-ethyl)-phenyl]-5-methyl-pyrazole

(80) 2-(4-amidino-phenyl)-5-[4-(2-carboxy-ethyl)-phenyl]-furan

(81) 2-(4-amidino-phenyl)-5-[4-(2-carboxy-ethyl)-phenyl]-tetrahydrofuran

(82) 3-(4-amidino-phenyl)-5-[4-(2-carboxy-ethyl)-phenyl]-isoxazole

(83) 4-(4-amidino-phenyl)-2-[4-(2-carboxy-ethyl)-phenyl]-5-methyl-imidazole

(84) 1-(4-amidino-2-fluoro-phenyl)-3-[4-(2-carboxy-ethyl)-phenyl]-2H-pyrazol-5-one

(85) 2-(4-amidino-phenyl)-5-[4-(2-carboxy-ethyl)-phenyl]-thiophene

(86) 3-(4-amidino-phenyl)-4-carboxy-5-[4-(2-carboxy-ethyl)-phenyl]-pyrazole

(87) 3-(4-amidino-phenyl)-4-aminocarbonyl-5-[4-(2-carboxy-ethyl)-phenyl]-pyrazole

(88) 2-[4-(2-carboxy-ethyl)-phenyl]-4-(3-guanidino-phenyl)-imidazole

(89) 1-(4-amidino-3'-methylthio-4'-biphenylyl)-4-(2-carboxy-ethyl)-imidazole

(90) 1-(4-amidino-3'-methylsulphinyl-4'-biphenylyl)-4-(2-carboxy-ethyl)-imidazole

(91) 1-(4-amidino-3'-methylsulphonyl-4'-biphenylyl)-4-(2-carboxy-ethyl)-imidazole

(92) 1-[5-(4-amidino-phenyl)-2-pyridyl]-4-(2-carboxy-ethyl)-imidazole

(93) 4-(4-amidino-phenyl)-2-[4-(2-carboxy-ethyl)-1-piperidinyl]-imidazole

(94) 4-(4-amidino-phenyl)-2-[4-(2-carboxy-vinyl)-phenyl]-imidazole

(95) 1-[6-(4-amidino-phenyl)-5-methyl-3-pyridazinyl]-4-(2-carboxy-ethyl)-imidazole

(96) 4-(2-carboxy-ethyl)-1-[6-(4-methylamidino-phenyl)-3-pyridazinyl]-imidazole

(97) 1-[6-(4-n-butylamidino-phenyl)-3-pyridazinyl]-4-(2-carboxy-ethyl)-imidazole

(98) 3-(4-amidino-4'-biphenylyl)-5-(2-carboxy-ethyl)-pyrazole

(99) 1-[6-(4-amidino-2-fluoro-phenyl)-3-pyridazinyl]-4-(2-carboxy-ethyl)-imidazole (100) 1-[6-(4-amidino-2-methoxy-phenyl)-3-pyridazinyl]-4-(2-carboxy-ethyl)-imidazole
(101) 4-(4-amidino-phenyl)-2-(4-carboxymethyloxy-phenyl)-imidazole
(102) 4-(4-amidino-phenyl)-2-(4-carboxymethylthio-phenyl)-imidazole
(103) 4-(4-amidino-phenyl)-2-(4-carboxymethylsulphinyl-phenyl)-imidazole
(104) 4-(4-amidino-phenyl)-2-(4-carboxymethylsulphonyl-phenyl)-imidazole
(105) 4-(4-amidino-phenyl)-2-(4-carboxymethylamino-phenyl)-imidazole
(106) 2-[4-(N-acetyl-N-carboxymethyl-amino)-phenyl]-4-(4-amidino-phenyl)-imidazole
(107) 2-[4-(N-acetyl-N-carboxymethyl-amino)-3-bromo-phenyl]-4-(4-amidino-phenyl)-imidazole
(108) 2-[4-(N-acetyl-N-carboxymethyl-amino)-3-fluoro-phenyl]-4-(4-amidino-phenyl)-imidazole
(109) 4-(4-amidino-phenyl)-2-(4-carboxymethyloxy-3-methyl-phenyl)-imidazole
(110) 4-(4-amidino-phenyl)-2-[4-(2-carboxy-ethyl)-3-nitro-phenyl]-imidazole
(111) 4-(4-amidino-phenyl)-2-[3-amino-4-(2-carboxy-ethyl)-phenyl]-imidazole
(112) 2-[3-acetylamino-4-(2-carboxy-ethyl)-phenyl]-4-(4-amidino-phenyl)-imidazole
(113) 4-(4-amidino-phenyl)-2-[3-benzoylamino-4-(2-carboxy-ethyl)-phenyl]-imidazole
(114) 4-(4-amidino-phenyl)-2-[4-(2-carboxy-ethyl)-3-methanesulphonylamino-phenyl]-imidazole
(115) 4-(4-amidino-phenyl)-2-[4-(2-carboxy-ethyl)-3-hydroxy-phenyl]-imidazole
(116) 4-(4-amidino-phenyl)-2-[4-(2-carboxy-ethyl)-3-methoxy-phenyl]-imidazole
(117) 4-(4-amidino-phenyl)-2-(4-carboxymethyloxy-3-methylthio-phenyl)-imidazole
(118) 4-(4-amidino-phenyl)-2-(4-carboxymethyloxy-3-methylsulphinyl-phenyl)-imidazole
(119) 4-(4-amidino-phenyl)-2-(4-carboxymethyloxy-3-methylsulphonyl-phenyl)-imidazole
(120) 4-(4-amidino-phenyl)-2-[4-(N-carboxymethyl-methylamino)-phenyl]-imidazole
(121) 4-(4-amidino-phenyl)-2-[1-(2-carboxy-ethyl)-2-oxo-4-pyridyl]-imidazole
(122) 4-(4-amidino-phenyl)-2-[2-(2-carboxy-ethyl)-5-pyridyl]-imidazole
(123) 4-(4-amidino-phenyl)-1-[6-(2-carboxy-ethyl)-3-pyridazinyl]-imidazole
(124) 4-(4-amidino-phenyl)-2-[4-(2-carboxy-ethyl)-cyclohexyl]-imidazole
(125) 4-(4-amidino-4'-biphenylyl)-2-(2-carboxy-ethyl)-imidazole
(126) 4-(4-amidino-4'-biphenylyl)-2-(2-carboxy-ethyl)-1-methyl-imidazole
(127) 2-(4-amidino-4'-biphenyl)-5-(2-carboxy-ethyl)-3-methoxycarbonyl-furan The mixture is reacted at 5° C. for 60 minutes.
Melting point: 251°–252° C. (decomp., sintering from 204° C.) $R_f$ value: 0.34 (silica gel; methylene chloride/methanol/glacial acetic acid=8:2:0.1)

(128) 2-(4-amidino-4'-biphenyl)-3-carboxy-5-(2-carboxy-ethyl)-furan

A four-molar excess of lithium hydroxide is used and the mixture is reacted for 6.5 hours at ambient temperature.
Melting point: 298° C. (decomp., sinters from 184° C.) $R_f$ value: 0.45 (silica gel; methylene chloride/methanol/glacial acetic acid=3:1:0.1)

(129) 4-[4-(1-amino-cyclopropyl)-phenyl]-2-[4-(2-carboxy-ethyl)-phenyl]-1-methyl-imidazole
(130) 4-[4-(1-amino-cyclopentyl)-phenyl]-2-[4-(2-carboxy-ethyl)-phenyl]-1-methyl-imidazole (131) 4-(4-amidino-phenyl)-2-[4-(1,3-bis-carboxy-2-propyl)-phenyl]-1-methyl-imidazole
(132) 4-(4-amidino-phenyl)-2-(3,4-dicarboxymethyloxy-phenyl)-1-methyl-imidazole
(133) 2-(4-amino-cyclohexyl)-4-[4-(2-carboxy-ethyl)-phenyl]-imidazole
(134) 4-(2-amino-2-carboxy-ethyl)-1-[6-(4-aminomethyl-phenyl)-3-pyridazinyl]-imidazole-dihydrochloride The amide is saponified with 1N sodium hydroxide solution at 100° C.
$R_f$ value: 0.32 (silica gel; methylene chloride/methanol/conc. ammonia=2:1:0.25)

(135) 1-[6-(4-amidino-phenyl)-3-pyridazinyl]-4-(2-carboxy-ethenyl)-imidazole
(136) 4-(4-amidino-phenyl)-2-[4-(2-carboxy-2-methyl-propyl)-phenyl]-1-methyl-imidazole
(137) 4-(4-aminomethyl-phenyl)-2-[4-(2-carboxy-ethyl)-phenyl]-1-methyl-imidazole
(138) 4-[4-(2-amino-ethyl)-phenyl]-2-[4-(2-carboxy-ethyl)-phenyl]-1-methyl-imidazole
(139) 4-[4-(1-amino-ethyl)-phenyl]-2-[4-(2-carboxy-ethyl)-phenyl]-1-methyl-imidazole
(140) 4-[4-(2-amino-2-propyl)-phenyl]-2-[4-(2-carboxy-ethyl)-phenyl]-1-methyl-imidazole
(141) 4-(1-amino-5-indanyl)-2-[4-(2-carboxy-ethyl)-phenyl]-1-methyl-imidazole
(142) 4-(1-amino-1,2,3,4-tetrahydro-6-naphthyl)-2-[4-(2-carboxy-ethyl)-phenyl]-1-methyl-imidazole
(143) 1-[6-(4-amidino-phenyl)-3-pyridazinyl]-4-(2-carboxy-propyl)-imidazole
(144) 4-(2-amino-2-carboxy-ethyl)-1-[4-(4-aminomethyl-piperidino)-phenyl]-imidazole
(145) 4-(2-amino-2-carboxy-ethyl)-1-[4-(4-aminomethyl-2-oxo-piperidino)-phenyl]-imidazole
(146) 3-(4-amidino-phenyl)-1-[4-(2-amino-2-carboxy-ethyl)-phenyl]-2H-pyrazol-5-one
(147) 2-[4-(2-carboxy-ethyl)-phenyl]-1-methyl-4-(4-methylaminomethyl-phenyl)-imidazole
(148) 2-[4-(2-carboxy-ethyl)-phenyl]-4-[4-(dimethylaminomethyl)-phenyl]-1-methyl-imidazole
(149) 4-(4-amino-cyclohexyl)-2-[4-[(2-carboxy-ethyl)-aminocarbonyl]-phenyl]-1-methyl-imidazole
(150) 2-[4-[(2-carboxy-ethyl)-aminocarbonyl]-phenyl]-1-methyl-4-(4-piperidinyl)-imidazole
(151) 2-[4-[(2-carboxy-ethyl)-aminocarbonyl]-phenyl]-1-methyl-4-(1-methyl-4-piperidinyl)-imidazole
(152) 1-[6-(4-amidino-phenyl)-3-pyridazinyl]-4-(2-carboxy-2-methoxy-ethyl)-imidazole
(153) 4-(4-amidino-phenyl)-2-[(4-(2-carboxy-ethyl)-phenyl]-1-(2-phenyl-ethyl)-imidazole

EXAMPLE 2

1-[6-(4-Amidino-phenyl)-3-pyridazinyl]-4-(2-methoxy-carbonyl-ethyl)-imidazole

A mixture of 1.1 g of 1-[6-(4-cyano-phenyl)-3-pyridazinyl]-4-(2-methoxycarbonyl-ethyl)-imidazole, 1500 ml of absolute methanol and 50 ml of methylene chloride is saturated with dry hydrogen chloride, whilst stirring and cooling with ice. The mixture is stirred for a further 16 hours at ambient temperature and the solvent is distilled off in vacuo. The residue is taken up in 250 ml of absolute methanol and mixed with 8 g of ammonium carbonate. The mixture is stirred for 30 minutes at ambient temperature, the precipitate is removed by suction filtering and the filtrate is evaporated down in vacuo. The evaporation residue is combined with the precipitate obtained previously and purified by column chromatography (eluant: methylene chloride/methanol/conc. ammonia=2:1:0.25).

Yield: 0.36 g (31% of theory), $R_f$ value: 0.22 (silica gel; methylene chloride/methanol/conc. ammonia=2:1:0.25) The following compounds are obtained analogously:

(1) 1-[6-(4-amidino-phenyl)-3-pyridazinyl]-4-(2-hydroxy-2-methoxycarbonyl-ethyl)-imidazole $R_f$ value: 0.17 (silica gel; methylene chloride/methanol/conc. ammonia=2:1:0.25)

(2) 1-[6-(4-amidino-phenyl)-3-pyridazinyl]-4-(2-amino-2-methoxycarbonyl-ethyl)-imidazole-tris-trifluoroacetate The starting product used is 1-[6-(4-cyano-phenyl)-3-pyridazinyl]-4-(2-tert.butyloxycarbonylamino-2-methoxycarbonyl-ethyl)-imidazole The crude free base is converted into the tris-trifluoroacetate by taking up in methylene chloride, adding trifluoroacetic acid, evaporating down and purifying over silica gel (eluant: methylene chloride/methanol/conc. ammonia 2:1:0.25).

$R_f$ value: 0.18 (silica gel; methylene chloride/methanol/conc. ammonia=2:1:0.25)

(3) 5-(4-amidino-phenyl)-2-[4-(2-methoxycarbonyl-ethyl)-phenyl]-tetrazole-hydrochloride $R_f$ value: 0.41 (silica gel; methylene chloride/methanol/conc. ammonia=4:1:0.25) Calculated x HCl: C 55.89 H 4.95 N 21.73 Cl 9.16 Found: 55.33 4.95 21.47 9.51

(4) 5-(4-amidino-4'-biphenylyl)-2-(2-methoxycarbonyl-ethyl)-tetrazole-hydrochloride $R_f$ value: 0.31 (silica gel; methylene chloride/methanol/conc. ammonia=4:1:0.25)

(5) 4-(4-amidino-phenyl)-2-[4-(2-methoxycarbonyl-ethyl)-phenyl]-thiazole-hydrochloride Melting point: 235°–238° C. $R_f$ value: 0.23 (Reversed phase plate RP8; 5% sodium chloride solution/methanol=4:6)

(6) 4-(4-amidino-phenyl)-2-[4-(2-methoxycarbonyl-ethyl)-phenyl]-1-methyl-imidazole-hydrochloride Melting point: 228°–230° C. (decomp.) $R_f$ value: 0.50 (silica gel; methylene chloride/methanol=4:1)

(7) 4-(4-amidino-phenyl)-2-[4-(2-methoxycarbonyl-ethyl)-phenyl]-imidazole-hydrochloride $R_f$ value: 0.60 (Reversed phase plate RP8; 5% sodium chloride solution/methanol=4:6) Calculated x 1.1 HCl x 0.5 H$_2$O: C 60.43 H 5.60 N 14.09 Cl 9.81 Found: 60.67 5.41 13.84 9.76

(8) 3-(4-amidino-phenyl)-5-[4-(2-methoxycarbonyl-ethyl)-phenyl]-1,2,4-triazole $R_f$ value: 0.11 (silica gel; methylene chloride/methanol=8.5:1.5)

(9) 2-(4-amidino-phenyl)-5-[4-(2-methoxycarbonyl-ethyl)-phenyl]-1,3,4-oxadiazole $R_f$ value: 0.37 (silica gel; methylene chloride/methanol=8:2)

(10) 2-(4-amidino-phenyl)-5-[4-(2-methoxycarbonyl-ethyl)-phenyl]-1,3,4-thiadiazole $R_f$ value: 0.45 (silica gel; methylene chloride/methanol=7:3)

(11) 1-[5-(4-amidino-phenyl)-2-pyrimidyl]-4-(2-amino-2-methoxycarbonyl-ethyl)-imidazole

(12) 1-[5-(4-amidino-phenyl)-4-methyl-2-pyrimidyl]-4-(2-amino-2-methoxycarbonyl-ethyl)-imidazole

(13) 1-[5-(4-amidino-phenyl)-2-pyrazinyl]-4-(2-amino-2-methoxycarbonyl-ethyl)-imidazole

(14) 1-[5-(4-amidino-phenyl)-4-methyl-2-pyrimidyl]-4-(2-methoxycarbonyl-ethyl)-imidazole

(15) 1-[5-(4-amidino-phenyl)-2-pyrimidyl]-4-(2-methoxycarbonyl-ethyl)-imidazole

(16) 1-(4-amidino-4'-biphenylyl)-4-(2-methoxycarbonyl-ethyl)-imidazole

(17) 4-(4-amidino-4'-biphenylyl)-2-(2-methoxycarbonyl-ethyl)-thiazole

(18) 5-(4-amidino-4'-biphenylyl)-2-(2-methoxycarbonyl-ethyl)-oxazole

(19) 2-(4-amidino-4'-biphenylyl)-5-(2-methoxycarbonyl-ethyl)-1,3,4-oxadiazole

(20) 2-(4-amidino-4'-biphenylyl)-5-(2-methoxycarbonyl-ethyl)-1,3,4-thiadiazole $R_f$ value: 0.09 (silica gel; methylene chloride/methanol=9:1)

(21) 2-(4-amidino-4'-biphenylyl)-4-(2-methoxycarbonyl-ethyl)-thiazole (22) 2-(4-amidino-4'-biphenylyl)-5-(2-methoxycarbonyl-ethyl)-thiophene

(23) 2-(4-amidino-4'-biphenylyl)-5-(2-methoxycarbonyl-ethyl)-furan

(24) 1-(4-amidino-3'-bromo-4'-biphenylyl)-4-(2-methoxycarbonyl-ethyl)-imidazole

(25) 1-[6-(4-amidino-phenyl)-3-pyridazinyl]-4-(2-methoxycarbonyl-ethyl)-2-methyl-imidzole

(26) 1-[6-(4-amidino-phenyl)-3-pyridazinyl]-2-isopropyl-4-(2-methoxycarbonyl-ethyl)-imidazole

(27) 1-[6-(4-amidino-phenyl)-3-pyridazinyl]-2-hexyl-4-(2-methoxycarbonyl-ethyl)-imidazole

(28) 1-[6-(4-amidino-phenyl)-3-pyridazinyl]-4-(2-methoxycarbonyl-ethyl)-imidazole

(29) 1-[6-(4-amidino-phenyl)-3-pyridazinyl]-4-(2-methoxycarbonyl-ethyl)-2-phenyl-imidazole

(30) 1-[6-(4-amidino-phenyl)-3-pyridazinyl]-4-(2-methoxycarbonyl-ethyl)-2-(3-pyridyl)-imidazole

(31) 3-(4-amidino-4'-biphenylyl)-5-(2-methoxycarbonyl-ethyl)-1,2,4-triazole

(32) 1-[6-(4-amidino-phenyl)-3-pyridazinyl]-4-(3-methoxycarbonyl-propyl)-imidazole

(33) 2-(4-amidino-3'-methoxy-4'-biphenylyl)-5-(2-methoxycarbonyl-ethyl)-1,3,4-thiadiazole

(34) 2-(4-amidino-3'-methyl-4'-biphenylyl)-5-(2-methoxycarbonyl-ethyl)-1,3,4-thiadiazole

(35) 1-[6-(4-amidino-phenyl)-3-pyridazinyl]-4-(2-dibenzylamino-2-methoxycarbonyl-ethyl)-imidazole $R_f$ value: 0.16 (silica gel; methylene chloride/methanol/conc. ammonia=4:1:0.25)

(36) 1-[6-(4-amidino-phenyl)-3-pyridazinyl]-2-(2-dimethylamino-2-methoxycarbonyl-ethyl)-imidazole

(37) 1-[6-(4-amidino-phenyl)-3-pyridazinyl]-3-(2-methoxycarbonyl-ethyl)-indole

Melting point: sinters from 160° C. $R_f$ value: 0.17 (silica gel; methylene chloride/methanol/conc. ammonia=4:1:0.25)

(38) 4-(4-amidino-4'-biphenylyl)-2-(2-methoxycarbonyl-ethyl)-5-methyl-thiazole

(39) 3-(4-amidino-4'-biphenylyl)-5-methoxycarbonyl-methylthio-1,2,4-triazole Melting point: 210° C. (sinters from 180° C.)

(40) 4-(4-amidino-4'-biphenylyl)-2-methoxycarbonyl-methylamino-thiazole

(41) 2-[1-(4-amidino-phenyl)-4-piperidinyl]-4-(2-methoxycarbonyl-ethyl)-thiazole

(42) 2-[4-(4-amidino-phenyl)-1-piperazinyl]-4-(2-methoxycarbonyl-ethyl)-thiazole

(43) 2-[1-(5-amidino-2-pyridyl)-4-piperidinyl]-4-(2-methoxycarbonyl-ethyl)-thiazole

(44) 1-[4-(5-amidino-2-pyrimidyl)-phenyl]-4-(2-methoxycarbonyl-ethyl)-imidazole

(45) 1-[4-(5-amidino-2-pyrazinyl)-phenyl]-4-(2-methoxycarbonyl-ethyl)-imidazole
(46) 1-[4-(4-amidino-phenyl)-cyclohexyl]-4-(2-methoxycarbonyl-ethyl)-imidazole
(47) 1-[6-(4-amidino-phenyl)-3-pyridazinyl]-3-(2,2-bis-methoxycarbonyl-ethyl)-indole
(48) 2-[1-(4-amidino-phenyl)-4-piperidinyl]-5-(2-methoxycarbonyl-ethyl)-1,3,4-oxadiazole
(49) 2-[1-(5-amidino-2-pyridyl)-4-piperidinyl]-5-(2-methoxycarbonyl-ethyl)-1,3,4-oxadiazole
(50) 5-[1-(4-amidino-phenyl)-4-piperidinyl]-2-(2-methoxycarbonyl-ethyl)-tetrazole
(51) 5-[1-(5-amidino-2-pyridyl)-4-piperidinyl]-2-(2-methoxycarbonyl-ethyl)-tetrazole
(52) 2-[6-(4-amidino-phenyl)-3-pyridazinyl]-4-(2-methoxycarbonyl-ethyl)-1,2,3-triazole
(53) 1-[6-(4-amidino-phenyl)-3-pyridazinyl]-4-(2-methoxycarbonyl-ethyl)-1,2,3-triazole
(54) 1-[6-(4-amidino-2-methyl-phenyl)-3-pyridazinyl]-4-(2-methoxycarbonyl-ethyl)-imidazole
(55) 2-(4-amidino-phenyl)-4-[4-(2-methoxycarbonyl-ethyl)-phenyl]-thiazole
(56) 2-(4-amidino-phenyl)-4-[4-(2-methoxycarbonyl-ethyl)-phenyl]-1-methyl-imidazole
(57) 5-(4-amidino-phenyl)-2-[4-(2-methoxycarbonyl-ethyl)-phenyl]-thiazole
(58) 2-(4-amidino-phenyl)-4-[4-(2-methoxycarbonyl-ethyl)-phenyl]-imidazole
(59) 1-(4-amidino-phenyl)-3-[4-(2-methoxycarbonyl-ethyl)-phenyl]-5-methyl-1,2,4-triazole
(60) 3-(4-amidino-phenyl)-5-[4-(2-methoxycarbonyl-ethyl)-phenyl]-pyrazole
(61) 5-(4-amidino-phenyl)-3-[4-(2-methoxycarbonyl-ethyl)-phenyl]-1-methyl-pyrazole
(62) 3-(4-amidino-phenyl)-5-[4-(2-methoxycarbonyl-ethyl)-phenyl]-1-phenyl-pyrazole
(63) 1-(4-amidino-phenyl)-4-[4-(2-methoxycarbonyl-ethyl)-phenyl]-2-methyl-imidazole
(64) 1-(4-amidino-phenyl)-4-[4-(2-methoxycarbonyl-ethyl)-phenyl]-2-phenyl-imidazole
(65) 4-(4-amidino-phenyl)-1-[4-(2-methoxycarbonyl-ethyl)-phenyl]-imidazole
(66) 1-(4-amidino-phenyl)-3-[4-(2-methxoycarbonyl-ethyl)-phenyl]-2H-pyrazol-5-one
(67) 1-(4-amidino-phenyl)-3-[4-(2-methoxycarbonyl-ethyl)-phenyl]-2-methyl-2H-pyrazole-5-one
(68) 3-(4-amidino-phenyl)-1-[4-(2-methoxycarbonyl-ethyl)-phenyl]-2H-pyrazol-5-one
(69) 3-(4-amidino-phenyl)-1-[4-(2-methoxycarbonyl-ethyl)-phenyl]-2-methyl-2H-pyrazole-5-one
(70) 1-(4-amidino-phenyl)-3-[4-(2-methoxycarbonyl-ethyl)-phenyl]-1,2,4-triazole
(71) 3-(4-amidino-phenyl)-1-[4-(2-methoxycarbonyl-ethyl)-phenyl]-1,2,4-triazole
(72) 4-(4-amidino-phenyl)-2-[4-(2-methoxycarbonyl-ethyl)-phenyl]-oxazole
(73) 4-(4-amidino-phenyl)-2-[4-(2-methoxycarbonyl-ethyl)-phenyl]-1-phenyl-imidazole
(74) 1-(4-amidino-phenyl)-3-[4-(2-methoxycarbonyl-ethyl)-phenyl]-pyrazole
(75) 1-(4-amidino-phenyl)-3-[4-(2-methoxycarbonyl-ethyl)-phenyl]-5-methyl-pyrazole
(76) 3-(4-amidino-phenyl)-1-[4-(2-methoxycarbonyl-ethyl)-phenyl]-pyrazole
(77) 3-(4-amidino-phenyl)-1-[4-(2-methoxycarbonyl-ethyl)-phenyl]-5-methyl-pyrazole
(78) 2-(4-amidino-phenyl)-5-[4-(2-methoxycarbonyl-ethyl)-phenyl]-furan
(79) 2-(4-amidino-phenyl)-5-[4-(2-methoxycarbonyl-ethyl)-phenyl]-tetrahydrofuran
(80) 3-(4-amidino-phenyl)-5-[4-(2-methoxycarbonyl-ethyl)-phenyl]-isoxazole
(81) 4-(4-amidino-phenyl)-2-[4-(2-methoxycarbonyl-ethyl)-phenyl]-5-methyl-imidazole
(82) 1-(4-amidino-2-fluoro-phenyl)-3-[4-(2-methoxycarbonyl-ethyl)-phenyl]-2H-pyrazol-5-one
(83) 2-(4-amidino-phenyl)-5-[4-(2-methoxycarbonyl-ethyl)-phenyl]-thiophene
(84) 3-(4-amidino-phenyl)-4-methoxycarbonyl-5-[4-(2-methoxycarbonyl-ethyl)-phenyl]-pyrazole
(85) 3-(4-amidino-phenyl)-4-aminocarbonyl-5-[4-(2-methoxycarbonyl-ethyl)-phenyl]-pyrazole
(86) 1-[6-(4-amidino-phenyl)-3-pyridazinyl]-4-[2-(5-tetrazolyl)-ethyl]-imidazole
(87) 1-[6-(4-amidino-phenyl)-3-pyridazinyl]-4-(2-phosphono-ethyl)-imidazole
(88) 1-[6-(4-amidino-phenyl)-3-pyridazinyl]-4-[2-(O-ethylphosphono)-ethyl]-imidazole
(89) 1-[6-(4-amidino-phenyl)-3-pyridazinyl]-4-(2-sulpho-ethyl)-imidazole
(90) 1-[6-(4-amidino-phenyl)-3-pyridazinyl]-4-(2-ethoxycarbonyl-ethyl)-imidazole The work is done with ethanolic hydrochloric acid.
(91) 1-(4-amidino-3'-methylthio-4'-biphenylyl)-4-(2-methoxycarbonyl-ethyl)-imidazole
(92) 1-(4-amidino-3'-methylsulphonyl-4'-biphenylyl)-4-(2-methoxycarbonyl-ethyl)-imidazole
(93) 1-[5-(4-amidino-phenyl)-2-pyridyl]-4-(2-methoxycarbonyl-ethyl)-imidazole
(94) 4-(4-amidino-phenyl)-2-[4-(2-methoxycarbonyl-ethyl)-1-piperidinyl]-imidazole
(95) 4-(4-amidino-phenyl)-2-[4-(2-methoxycarbonyl-vinyl)-phenyl]-imidazole
(96) 1-[6-(4-amidino-phenyl)-5-methyl-3-pyridazinyl]-4-(2-methoxycarbonyl-ethyl)-imidazole
(97) 4-(2-methoxycarbonyl-ethyl)-1-[6-(4-methylamidino-phenyl)-3-pyridazinyl]-imidazole The iminoester is taken up in absolute methanol and reacted with a 20-fold excess of a methanolic methylamine solution.
(98) 1-[6-(4-n-butylamidino-phenyl)-3-pyridazinyl]-4-(2-methoxycarbonyl-ethyl)-imidazole Prepared analogously to (97) with n-butylamine.
(99) 3-(4-amidino-4'-biphenylyl)-5-(2-methoxycarbonyl-ethyl)-pyrazole
(100) 1-[6-(4-amidino-2-fluoro-phenyl)-3-pyridazinyl]-4-(2-methoxycarbonyl-ethyl)-imidazole
(101) 1-[6-(4-amidino-2-methoxy-phenyl)-3-pyridazinyl]-4-(2-methoxycarbonyl-ethyl)-imidazole
(102) 4-(4-amidino-phenyl)-2-(4-methoxycarbonyloxy-phenyl)-imidazole
(103) 4-(4-amidino-phenyl)-2-(4-methoxycarbonylmethylthio-phenyl)-imidazole
(104) 4-(4-amidino-phenyl)-2-(4-methoxycarbonylmethylsulphonylphenyl)-imidazole
(105) 4-(4-amidino-phenyl)-2-(4-methoxycarbonylmethylamino-phenyl)-imidazole
(106) 2-[4-(N-acetyl-N-methoxycarbonylmethyl-amino)-phenyl]-4-(4-amidino-phenyl)-imidazole
(107) 2-[4-(N-acetyl-N-methoxycarbonylmethyl-amino)-3-bromo-phenyl]-4-(4-amidino-phenyl)-imidazole
(108) 2-[4-(N-acetyl-N-methoxycarbonylmethyl-amino)-3-fluoro-phenyl]-4-(4-amidino-phenyl)-imidazole
(109) 4-(4-amidino-phenyl)-2-(4-methoxycarbonyl-methyloxy-3-methyl-phenyl)-imidazole (110) 4-(4-amidino-phenyl)-2-[4-(2-methoxycarbonyl-ethyl)-3-nitro-phenyl)-imidazole
(111) 4-(4-amidino-phenyl)-2-[3-amino-4-(2-methoxycarbonyl-ethyl)-phenyl]-imidazole
(112) 2-[3-acetylamino-4-(2-methoxycarbonyl-ethyl)-phenyl]-4-(4-amidino-phenyl-imidazole
(113) 4-(4-amidino-phenyl)-2-[3-benzoylamino-4-(2-methoxycarbonyl-ethyl)-phenyl]-imidazole
(114) 4-(4-amidino-phenyl)-2-[3-methanesulphonylamino-4-(2-methoxycarbonyl-ethyl)-phenyl]-imidazole
(115) 4-(4-amidino-phenyl)-2-[3-hydroxy-4-(2-methoxycarbonyl-ethyl)-phenyl]-imidazole
(116) 4-(4-amidino-phenyl)-2-[3-methoxy-4-(2-methoxycarbonyl-ethyl)-phenyl]-imidazole
(117) 4-(4-amidino-phenyl)-2-(4-methoxycarbonyl-methyloxy-3-methylthio-phenyl)-imidazole
(118) 4-(4-amidino-phenyl)-2-(4-methoxycarbonyl-methyloxy-3-methylsulphonyl-phenyl)-imidazole
(119) 4-(4-amidino-phenyl)-2-[4-(N-methoxycarbonyl-methyl-methylamino)-phenyl)-imidazole
(120) 4-(4-amidino-phenyl)-2-[1-(2-methoxycarbonyl-ethyl)-2-oxo-4-pyridyl]-imidazole
(121) 4-(4-amidino-phenyl)-2-[2-(2-methoxycarbonyl-ethyl)-5-pyridyl]-imidazole
(122) 4-(4-amidino-phenyl)-1-[6-(2-methoxycarbonyl-ethyl)-3-pyridazinyl]-imidazole
(123) 4-(4-amidino-phenyl)-2-[4-(2-methoxycarbonyl-ethyl)-cyclohexyl]-imidazole
(124) 4-(4-amidino-4'-biphenylyl)-2-(2-methoxycarbonyl-ethyl)-1-methyl-imidazole
(125) 4-(4-amidino-4'-biphenylyl)-2-(2-methoxycarbonyl-ethyl)-imidazole
(126) 2-(4-amidino-4'-biphenylyl)-3-methoxycarbonyl-5-(2-methoxycarbonyl-ethyl)-furan-hydrochloride $R_f$ value: 0.52 (silica gel; methylene chloride/methanol= 8:2)

(127) 4-(4-amidino-phenyl)-2-[4-(1,3-dimethoxycarbonyl-2-propyl)-phenyl]-1-methyl-imidazole
(128) 4-(4-amidino-phenyl)-2-[3,4-bis(methoxycarbonyl-methyloxy)-phenyl]-1-methyl-imidazole
(129) 1-[6-(4-amidino-phenyl)-3-pyridazinyl]-4-(2-methoxycarbonyl-ethenyl)-imidazole
(130) 4-(4-amidino-phenyl)-2-[4-(2-methoxycarbonyl-2-methyl-propyl)-phenyl]-1-methyl-imidazole
(131) 1-[6-(4-amidino-phenyl)-3-pyridazinyl]-4-(2-methoxycarbonyl-propyl)-imidazole
(132) 3-(4-amidino-phenyl)-1-[4-(2-amino-2-methoxycarbonyl-ethyl)-phenyl]-2H-pyrazol-5-one
(133) 1-[6-(4-amidino-phenyl)-3-pyridazinyl]-4-(2-methoxy-2-methoxycarbonyl-ethyl)-imidazole
(134) 4-(4-amidino-phenyl)-2-[4-(2-methoxycarbonyl-ethyl)-phenyl]-1-(2-phenyl-ethyl)-imidazole

EXAMPLE 3

1-[6-(4-Cyano-phenyl)-3-pyridazinyl]-4-(2-methoxycarbonyl-ethyl)-imidazole

A mixture of 2.15 g of 3-chloro-6-(4-cyano-phenyl)-pyridazine, 2.1 g of methyl 3-(4-imidazolyl)-propionate, 2 g of potassium carbonate and 4 ml of dimethylsulphoxide is stirred for 3 hours at 130° C. under argon. The reaction mixture is stirred into water and extracted with methylene chloride. The product which remains undissolved is filtered off. A further fraction is obtained by evaporating the methylene chloride phase and chromatographing the residue over silica gel (eluant: methylene chloride/methanol=9:1). The two fractions are combined and further processed without any additional purification.

yield: 1.2 g (36% of theory) $R_f$ value: 0.53 (silica gel; methylene chloride/methanol=9:1) The following compounds are obtained analogously:

(1) 1-[6-(4-cyano-phenyl)-3-pyridazinyl]-4-(2-hydroxy-2-methoxycarbonyl-ethyl)-imidazole $R_f$ value: 0.46 (silica gel; methylene chloride/methanol= 9:1)

(2) 1-[6-(4-cyano-phenyl)-3-pyridazinyl]-4-(2-tert.butyloxycarbonylamino-2-methoxycarbonyl-ethyl)-imidazole The work is done in dimethylformamide with sodium hydride as base at ambient temperature.

Melting point: 170°–185° C. (decomp.) $R_f$ value: 0.23 (silica gel; methylene chloride/methanol=40:1)

(3) 1-[6-(4-cyano-phenyl)-3-pyridazinyl]-3-(2-methoxycarbonylethyl)-indole.

The work is done in dimethylformamide with sodium hydride as base at ambient temperature.

$R_f$ value: 0.86 (silica gel; methylene chloride/methanol= 9:1)

(4) 4-(2-tert.butyloxycarbonylamino-2-methoxycarbonyl-ethyl)-1-[6-(4-methoxycarbonylamidino-phenyl)-3-pyridazinyl]-imidazole $R_f$ value: 0.29 (silica gel; methylene chloride/methanol= 15:1)

EXAMPLE 4

1-[6-(4-Methoxycarbonylamidino-phenyl)-3-pyridazinyl]-4-(2-methoxycarbonyl-ethyl)-imidazole 0.35 g of 1-[6-(4-amidino-phenyl)-3-pyridazinyl]-4-(2-methoxycarbonyl-ethyl)-imidazole are dissolved in a mixture of 25 ml of methanol and 20 ml of methylene chloride. 0.62 g of methylchloroformate are added and the pH is maintained between 8.5 and 9 by the addition of 1N sodium hydroxide solution. After the starting material has disappeared, the solvent is distilled off in vacuo, water is added and the mixture is extracted with methylene chloride. The residue remaining after evaporation of the organic phases is purified by column chromatography over silica gel (eluant: methylene chloride/methanol=20:1).

Yield: 0.05 g (12% of theory), $R_f$ value: 0.43 (silica gel; methylene chloride/methanol=9:1) The following compounds are obtained analogously:

(1) 4-(4-methoxycarbonylamidino-phenyl)-2-[4-(2-methoxycarbonyl-ethyl)-phenyl]-1-methyl-imidazole $R_f$ value: 0.50 (Reversed phase plate RP8; 5% sodium chloride solution/methanol=4:6)

(2) 4-(4-methoxycarbonylamidino-phenyl)-2-[4-(2-methoxycarbonyl-ethyl)-phenyl]-imidazole $R_f$ value: 0.53 (Reversed phase plate RP8; 5% sodium chloride solution/methanol=4:6)

(3) 1-[6-(4-ethoxycarbonylamidino-phenyl)-3-pyridazinyl]-4-(2-ethoxycarbonyl-ethyl)-imidazole $R_f$ value: 0.53 (silica gel; methylene chloride/methanol= 9:1)

(4) 4-(2-dibenzylamino-2-methoxycarbonyl-ethyl)-1-[6-(4-methoxycarbonylamidino-phenyl)-3-pyridazinyl]-imidazole-hydrochloride $R_f$ value: 0.53 (silica gel; methylene chloride/methanol= 9:1) Calculated x HCl: C 63.79 H 5.35 N 15.32 Found: 63.58 5.43 15.26

(5) 1-[6-(4-methoxycarbonylamidino-phenyl)-3-pyridazinyl]-4-(2-methoxycarbonyl-2-methoxycarbonylamino-ethyl)-imidazole (6) 5-(4-methoxycarbonylamidino-4'-biphenylyl)-2-(2-methoxycarbonyl-ethyl)-tetrazole $R_f$ value: 0.89 (silica gel; methylene chloride/methanol/conc. ammonia=4:1:0.25)

(7) 2-(4-methoxycarbonylamidino-4'-biphenylyl)-5-(2-methoxycarbonyl-ethyl)-1,3,4-thiadiazole (8) 5-(2-isopropyloxycarbonyl-ethyl)-2-(4-methoxycarbonylamidino-4'-biphenylyl)-1,3,4-thiadiazole (9) 4-[4-[(1-acetoxy-ethyl)-oxycarbonylamidino]-phenyl]-2-[4-(2-methoxycarbonyl-ethyl)-phenyl]-1-methyl-imidazole The work is done in methylene chloride with N-ethyldiisopropylamine

(10) 4-[4-(acetoxymethyloxycarbonylamidino)-phenyl]-2-[4-(2-methoxycarbonyl-ethyl)-phenyl]- 1-methyl-imidazole The work is done in methylene chloride with N-ethyldiisopropylamine

(11) 1-[6-[4-(acetoxymethyloxycarbonylamidino)-phenyl]-3-pyridazinyl]-4-(2-methoxycarbonyl-ethyl)-imidazole The work is done in methylene chloride with N-ethyldiisopropylamine

(12) 2-[4-(acetoxymethyloxycarbonylamidino)-4'-biphenylyl]-5-(2-methoxycarbonyl-ethyl)- 1,3,4-thiadiazole The work is done in methylene chloride with N-ethyldiisopropylamine

(13) 4-[4-(butyryloxymethyloxycarbonylamidino)-phenyl]-2-[4-(2-methoxycarbonyl-ethyl)-phenyl]-1-methyl-imidazole The work is done in methylene chloride with N-ethyldiisopropylamine

(14) 4-(4-allyloxycarbonylamidino-phenyl)-2-[4-(2-methoxycarbonyl-ethyl)-phenyl]-1-methyl-imidazole

(15) 4-[4-(2-cyclohexyloxycarbonyl-ethyl)-phenyl]-4-(4-methoxycarbonylamidino-phenyl)-1-methyl-imidazole

(16) 4-[4-(2-cyclopentyloxycarbonyl-ethyl)-phenyl]-4-(4-methoxycarbonylamidino-phenyl)-1-methyl-imidazole

(17) 4-(4-methoxycarbonylamidino-phenyl)-1-methyl-2-[4-[2-[(2-phenyl-ethyl)-oxycarbonyl]-ethyl]-phenyl]-imidazole

EXAMPLE 5

5-(4-Cyano-phenyl)-2-[4-(2-methoxycarbonyl-ethyl)-phenyl]-tetrazole 2.16 g of methyl 3-(4-amino-phenyl)-propionate are dissolved in a mixture of 8 ml of water, 8 ml of ethanol and 2.6 ml of conc. hydrochloric acid, cooled to 0° C., a solution of 0.7 g sodium nitrite in 4 ml of water is added dropwise and the resulting mixture is stirred for a further 20 minutes at 0° C. The resulting solution is added dropwise to a solution, cooled to −15° C., of 2.85 g of 4-cyano-benzaldehyde-benzenesulphonylhydrazone in 60 ml of pyridine over a period of 30 minutes. The mixture is stirred for a further 30 minutes at −15° C., diluted with water and extracted with methylene chloride. The organic phases are washed with dilute hydrochloric acid and water and evaporated down. The crude product remaining is purified by column chromatography over silica gel (eluant: methylene chloride/methanol=50:1).

Yield: 2.8 g (84% of theory), $R_f$ value: 0.53 (silica gel; cyclohexane/ethyl acetate=2:1)

EXAMPLE 6

5-(4-Cyano-4'-biphenylyl)-2-(2-methoxycarbonyl-ethyl)-tetrazole 1 g of 5-(4-cyano-4'-biphenylyl)-tetrazole, 15 ml of ethanol and 0.45 g of potassium tert.butoxide are refluxed together and 0.44 ml of methyl 3-bromo-propionate are added. The mixture is heated for a further 16 hours, cooled to ambient temperature and the precipitate formed is washed with water.

Yield: 0.4 g (30% of theory), $R_f$ value: 0.69 (silica gel; methylene chloride/methanol/glacial acetic acid=15:1:0.2)

The following compounds are obtained analogously:

(1) 4-(4-cyano-phenyl)-2-[4-(2-methoxycarbonyl-ethyl)-phenyl]-1-methyl-imidazole Sodium hydride is used as the base and dimethylformamide as the solvent Melting point: 107°–109° C. $R_f$ value: 0.60 (silica gel; methylene chloride/ethyl acetate/cyclohexane=5:2:1)

(2) 3-(4-cyano-4'-biphenylyl)-5-methoxycarbonylmethylthio-1,2,4-triazole

The work is done in methanol.

Melting point: 206°–208° C. $R_f$ value: 0.70 (silica gel; ethyl acetate/petroleum ether=7:3)

EXAMPLE 7

4-(4-Cyano-phenyl)-2-[4-(2-methoxycarbonyl-ethyl)-phenyl]-thiazole 5.3 g of 4-(2-methoxycarbonyl-ethyl)-thiobenzoic acid amide and 5.4 g of 2-bromo-4'-cyano-acetophenone are dissolved in 500 ml of methanol, refluxed for 24 hours and then stirred for 40 hours at ambient temperature. The precipitate formed is taken up in 200 ml of ethyl acetate, extracted with semisaturated potassium carbonate solution, water and saturated common salt solution and evaporated down.

Yield: 3.0 g (36% of theory), Melting point: 124° C. $R_f$ value: 0.27 (silica gel; cyclohexane/ethyl acetate=4:1) The following compound is obtained analogously:

(1) 4-(4-cyano-phenyl)-2-[4-(2-methoxycarbonyl-ethyl)-phenyl]-imidazole

The work is done in dioxane and sodium carbonate is added as the base. The starting material used is 4-(2-methoxycarbonyl-ethyl)-benzamidine-hydrochloride Melting point: 137°–139° C. $R_f$ value: 0.50 (silica gel; methylene chloride/ethyl acetate/cyclohexane=5:2:1)

EXAMPLE 8

2-(4-Cyano-phenyl)-5-[4-(2-methoxycarbonyl-ethyl)-phenyl]-1,3,4-thiadiazole

A mixture of 1.9 g of N-(4-cyano-benzoyl)-N'-[4-(2-methoxycarbonyl-ethyl)-benzoyl]-hydrazine, 2.35 g of 2,4-bis-(4-methoxy-phenyl)-1,3-dithia-2,4-diphosphetane-2,4-disulphide and 35 ml of tetrahydrofuran is refluxed for one hour with stirring. After cooling, the mixture is poured onto a solution of 1.8 sodium hydroxide in 135 ml of ice water, the precipitate formed is filtered off and washed with water.

Yield: 1 g (53% of theory), $R_f$ value: 0.93 (silica gel; methylene chloride/methanol=19:1) The following compound is obtained analogously:

(1) 2-(4-cyano-4'-biphenylyl)-5-(2-methoxycarbonyl-ethyl)-1,3,4-thiadiazole $R_f$ value: 0.90 (silica gel; methylene chloride/methanol=9:1)

EXAMPLE 9

3-(4-Cyano-phenyl)-5-[4-(2-methoxycarbonyl-ethyl)-phenyl]-1,2,4-triazole 3.0 g of methyl 4-(2-methoxycarbonyl-ethyl)-iminobenzoate (prepared from 4-(2-methoxycarbonyl-ethyl)-benzonitrile and methanolic hydrochloric acid), 2.0 g of 4-cyano-benzohydrazide and 45 ml of pyridine are heated to 50° C.

for 6 hours. The mixture is poured onto 250 ml of water, extracted with 150 ml of methylene chloride, the organic phase is washed with water and 2N hydrochloric acid, evaporated down, and the residue is separated, by chromatography on silica gel, into the components (eluant: methylene chloride/methanol=9:1).

Yield: 1.0 g (22% of theory), $R_f$ value: 0.68 (silica gel; methylene chloride/methanol=8:2) The following compound is obtained analogously:
(1) 2-(4-cyano-phenyl)-5-[4-(2-methoxycarbonyl-ethyl)-phenyl]-1,3,4-oxadiazole The compound is obtained as one of the by-products in the mixture described above.

$R_f$ value: 0.91 (silica gel; methylene chloride/methanol= 8:2)

EXAMPLE 10

4-(2-Amino-2-aminocarbonyl-ethyl)-1-[6-(4-aminomethyl-phenyl)-3-pyridazinyl]-imidazole 1.9 g of 4-(2-amino-2-methoxycarbonyl-ethyl)-1-[6-(4-cyanophenyl)-3-pyridazinyl] -imidazole are hydrogenated in 300 ml of methanolic ammonia in the presence of 0.5 g of Raney nickel using 5 bars of hydrogen at ambient temperature for 12 hours. The catalyst is separated off by filtering, the filtrate is evaporated down in vacuo and the residue is purified by chromatography on silica gel (eluant: methylene chloride/methanol/conc. ammonia=1:1:0.1).

Yield: 0.45 g (24% of theory), $R_f$ value: 0.41 (silica gel; methylene chloride/methanol/conc. ammonia=4:1:0.25) The following compounds are obtained analogously:
(1) 4-[4-(2-amino-ethyl)-phenyl]-2-[4-(2-methoxycarbonyl-ethyl)-phenyl]-1 -methyl-imidazole 10% palladium/charcoal is used and the work is done in a 10:1 mixture of methanol and methanolic hydrochloric acid.
(2) 4-(4-aminomethyl-phenyl)-2-[4-(2-methoxycarbonyl-ethyl)-phenyl]-1-methyl-imidazole The same procedure is used as in (1).
(3) 1-[6-(4-aminomethyl-phenyl)-3-pyridazinyl]-4-(2-methoxycarbonyl-ethyl)-imidazole-hydrochloride The same procedure is used as in (1).

EXAMPLE 11

4-[4-(1-Amidino-4-piperidinyl)-phenyl]-2-(2-methoxycarbonyl-ethyl)-thiazole

Prepared from 2-(2-methoxycarbonyl-ethyl)-4-[4-(4-piperidinyl)-phenyl]-thiazole and S-ethylisothiourea-hydrobromide by heating to 100° C. for 4 hours in dimethylformamide in the presence of sodium carbonate.

EXAMPLE 12

1-(4-Amidino-3'-methylsulphinyl-4'-biphenylyl)-4-(2-methoxycarbonyl-ethyl)-imidazole Prepared by oxidation of 1-(4-amidino-3'-methylthio-4'-biphenylyl)-4-(2-methoxycarbonyl-ethyl)-imidazole with hydrogen peroxide in glacial acetic acid. The following compounds are obtained analogously:
(1) 4-(4-amidino-phenyl)-2-(4-methoxycarbonylmethyloxy-3 -methylsulphinyl-phenyl)-imidazole
(2) 4-(4-amidino-phenyl)-2-(4-methoxycarbonylmethyl-sulphinyl-phenyl)-imidazole

EXAMPLE 13

1-[6-(4-Amidino-phenyl)-3-pyridazinyl]-4-(2-n-butyloxycarbonyl-ethyl)-imidazole

Prepared from 1-[6-(4-amidino-phenyl)-3-pyridazinyl]-4-(2-methoxycarbonyl-ethyl)-imidazole by stirring for three days at ambient temperature with saturated n-butanolic hydrochloric acid. The following compounds are obtained analogously:
(1) 4-(4-amidino-phenyl)-2-[4-(2-cyclohexyloxycarbonyl-ethyl)-phenyl]-1-methyl-imidazole
(2) 4-(4-amidino-phenyl)-2-[4-(2-cyclopentyloxycarbonyl-ethyl)-phenyl]-1-methyl-imidazole
(3) 4-(4-amidino-phenyl)-2-[4-(2-cyclooctyloxycarbonyl-ethyl)-phenyl]-1-methyl-imidazole
(4) 4-(4-amidino-phenyl)-2-[4-(2-cyclohexylmethyloxycarbonyl-ethyl)-phenyl]- 1-methyl-imidazole
(5) 4-(4-amidino-phenyl)-1-methyl-2-[4-[2-(2-phenyl ethyloxycarbonylethyl]-phenyl]-imidazole

EXAMPLE 14

2-(4-Cyano-4'-biphenylyl)-3-ethoxycarbonyl-5-(2-ethoxycarbonyl-ethyl)-furan 6.2 g of ethyl 7-(4-cyano-4'-biphenyl)-6-ethoxycarbonyl-4,7 -dioxo-heptanoate are treated with 8.2 g of phosphorus pentoxide in 250 ml of toluene over a steam bath for 6 hours. The precipitate is filtered off, washed three times with 150 ml of hot toluene and the filtrate is evaporated down in vacuo. The residue is triturated in crystalline form with ether, filtered off and washed with ether. Another fraction is obtained from the mother liquors.

Yield: 4.4 g (70% of theory), Melting point: 115°–116° C. $R_f$ value: 0.61 (silica gel; ethyl acetate/cyclohexane=1:2.5, developed twice)

EXAMPLE 15

4-(3-Guanidino-phenyl)-2-[4-(2-methoxycarbonyl-ethyl)-phenyl] -imidazole-hydrochloride Prepared from 4-(3-amino-phenyl)-2-[4-(2-methoxycarbonyl-ethyl)-phenyl]-imidazole-hydrochloride by refluxing for three hours with cyanamide in dioxane.

EXAMPLE 16

2-[4-[(2-Methoxycarbonyl-ethyl)-aminocarbonyl]-phenyl]-1-methyl-4-(4-piperidinyl)-imidazole Prepared by treating 4-(1-benzyloxycarbonyl-4-piperidinyl)-2-[4-[(2-methoxycarbonyl-ethyl)-aminocarbonyl]-phenyl]-1-methyl-imidazole with 3 bars of hydrogen in the presence of 5% palladium/charcoal in methanol. The following compounds are obtained analogously:
(1) 4-(4-amino-cyclohexyl)-2-[4-[(2-methoxycarbonyl-ethyl)-aminocarbonyl]-phenyl]- 1-methyl-imidazole
(2) 2-[4-(2-methoxycarbonyl-ethyl)-phenyl]-1-methyl-4-(4-methylaminomethyl-phenyl)-imidazole
(3) 2-(4-amino-cyclohexyl)-4-[4-(2-methoxycarbonyl-ethyl)-phenyl]-imidazole
(4) 4-(4-amidino-phenyl)-1-methyl-2-[4-[2-(pivaloyloxymethylozycarbonyl)-ethyl]-phenyl]-imidazole
(5) 4-(4-amidino-phenyl)-2-[4-[2-[(1-ethoxycarbonyloxyethyl)-oxycarbonyl] -ethyl]-phenyl]-1-methyl-imidazole
(6) 4-(4-amidino-phenyl)-2-[4-[2-[(1-cyclohexyloxy-carbonyloxyethyl)-oxycarbonyl]-ethyl]-phenyl]-1-methyl-imidazole
(7) 2-[4-[2-(acetoxymethyloxycarbonyl)-ethyl]-phenyl]-4-(4-amidino-phenyl)-1 -methyl-imidazole
(8) 4-(4-amidino-phenyl)-2-[4-[2-(butyryloxymethyloxycarbonyl]-ethyl]-phenyl]-1 -methyl-imidazole
(9) 4-(4-amidino-phenyl)-2-[4-[2-(isobutyryloxymethyloxycarbonyl)-ethyl]-phenyl]-1 -methyl-imidazole
(10) 4-(4-amidino-phenyl)-2-[4-[2-(benzoyloxymethyloxycarbonyl)-ethyl]-phenyl]-1-methyl-imidazole

(11) 1-[6-(4-amidino-phenyl)-3-pyridazinyl]-4-[2-[(cyclohexyloxycarbonyloxymethyl)-oxycarbonyl]-ethyl]-imidazole
(12) 2-(4-amidino-4'-biphenylyl)-5-[2-[(cyclohexyloxycarbonyloxymethyl)-oxycarbonyl]-ethyl] -1,3,4,-thiadiazole
(13) 1-[6-(4-amidino-phenyl)-3-pyridazinyl]-4-[2-[(1 -ethoxycarbonyloxy-ethyl)-oxycarbonyl]-ethyl]-imidazole
(14) 2-(4-amidino-4'-biphenylyl)-5-[2-[(1-ethoxycarbonyloxy-ethyl)-oxycarbonyl]-ethyl] -1,3,4-thiadiazole
(15) 1-[6-(4-amidino-phenyl)-3-pyridazinyl]-4-[2 -(pivaloyloxymethyloxycarbonyl)-ethyl]-imidazole
(16) 2-(4-amidino-4'-biphenylyl)-5-[2-(pivaloyloxymethyloxycarbonyl)-ethyl] -1,3,4-thiadiazole

EXAMPLE 17

4-(2-Amino-2-methoxycarbonyl-ethyl)-1-[6-(4-cyano-phenyl)-3-pyridazinyl]-imidazole A solution of 3.1 g of 4-(2-tert.butyloxycarbonylamino-2 -methoxycarbonyl-ethyl)-1-[6-(4-cyano-phenyl)-3-pyridazinyl]-imidazole in 50 ml of methylene chloride is cooled to 0° C. and mixed with 20 ml of trifluoroacetic acid. The mixture is stirred for 16 hours at ambient temperature, evaporated down in vacuo at ambient temperature and the residue is purified by chromatography on silica gel (eluant: methylene chloride/methanol/conc. ammonia=10:1:0.1)

Yield: 1.9 g (79% of theory) Melting point: 110°–112° C. $R_f$ value: 0.37 (silica gel; methylene chloride/methanol/conc. ammonia=10:1:0.1) The following compounds are obtained analogously:
(1) 4-[4-(1-amino-cyclopentyl)-phenyl]-2-[4-(2-methoxycarbonyl-ethyl)-phenyl]-1 -methyl-imidazole
(2) 4-(2-amino-2-methoxycarbonyl-ethyl)-1-[4-(4-aminomethyl-piperidino)-phenyl]-imidazole
(3) 4-(2-amino-2-methoxycarbonyl-ethyl)-1-[4-(4-aminomethyl-2 -oxo-piperidino)-phenyl]-imidazole
(4) 4-[4-(1-amino-cyclopropyl)-phenyl]-2-[4-(2-methoxycarbonyl-ethyl)-phenyl]-1 -methyl-imidazole

EXAMPLE 18

4-[4-(2-Amino-2-propyl)-phenyl]-2-[4-(2-methoxycarbonyl-ethyl)-phenyl]-1-methyl-imidazole Prepared from 4-[4-(2-aminocarbonyl-2-propyl)-phenyl]-2-[4-(2 -methoxycarbonyl-ethyl)-phenyl]-1-methyl-imidazole by treating with [bis(trifluoroacetoxy)iodo]benzene in acetonitrile/water at ambient temperature.

EXAMPLE 19

4-[4-(1-Amino-ethyl)-phenyl]-2-[4-(2-methoxycarbonyl-ethyl)-phenyl]-1-methyl-imidazole Prepared from 4-[4-(1-hydroxyimino-ethyl)-phenyl]-2-[4-(2 -methoxycarbonyl-ethyl)-phenyl]-1-methyl-imidazole by reducing with 5 bars of hydrogen in a 50:1-mixture of methanol and methanolic hydrochloric acid at ambient temperature in the presence of 10% palladium/charcoal. The following compounds are obtained analogously:
(1) 4-(1-amino-5-indanyl)-2-[4-(2-methoxycarbonyl-ethyl)-phenyl]-1-methyl-imidazole
(2) 4-(1-amino-1,2,3,4-tetrahydro-6-naphthyl)-2-[4-(2 -methoxycarbonyl-ethyl)-phenyl]-1-methyl-imidazole

EXAMPLE 20

1-[6-(4-Amidino-phenyl)-3-pyridazinyl]-4-(2-hydroxy-2 -methoxycarbonyl-ethyl)-imidazole-hydrochloride A mixture of 0.07 g of 1-[6-(4-amidino-phenyl)-3-pyridazinyl]-4-(2-carboxy-2-hydroxy-ethyl)-imidazole, 100 ml of methanol and 20 ml of methanolic hydrochloric acid is stirred at ambient temperature for 3 hours and then evaporated down in vacuo.

Yield: 0.08 g (100% of theory), Melting point: sinters from 240° C. $R_f$ value: 0.17 (silica gel; methylene chloride/methanol/conc. ammonia=2:1:0.25) The following compounds are obtained analogously:
(1) 4-(2-amino-2-methoxycarbonyl-ethyl)-1-[6-(4 -aminomethyl-phenyl)-3-pyridazinyl]-imidazole
(2) 2-(4-amidino-4'-biphenylyl)-5-(2-isopropyloxycarbonyl-ethyl)-1,3,4-thiadiazole The associated methylester is used as starting material and the work is done in isopropanolic hydrochloric acid.

EXAMPLE 21

4-[4-(Dimethylaminomethyl)-phenyl]-2-[4-(2-methoxycarbonyl-ethyl)-phenyl]-1-methyl-imidazole Prepared from 4-(4-aminomethyl-phenyl)-2-[4-(2-methoxycarbonyl-ethyl)-phenyl]-1-methyl-imidazole by treating with formaldehyde and sodium cyanoborohydride. The following compound is obtained analogously:
(1) 2-[4-[(2-methoxycarbonyl-ethyl)-aminocarbonyl]-phenyl]-1 -methyl-4-(1-methyl-4-piperidinyl)-imidazole

EXAMPLE 22

1-[6-(4-Cyano-phenyl)-3-pyridazinyl]-4-(2-dibenzylamino-2 -methoxycarbonyl-ethyl)-imidazole 1.1 g of 4-(2-amino-2-methoxycarbonyl-ethyl)-1-[6-(4-cyano-phenyl)-3-pyridazinyl] -imidazole is dissolved in 20 ml of methylene chloride, 60 ml of benzylchloride and 10 ml of triethylamine are added and the mixture is stirred for 6 hours at 75°–80° C. It is evaporated down in vacuo, mixed with water and extracted with ethyl acetate. The ethyl acetate phase is evaporated down and the residue is purified by chromatography over silica gel (eluant: methylene chloride/methanol=20:1).

Yield: 0.55 g (32% of theory), $R_f$ value: 0.93 (silica gel; methylene chloride/methanol/conc. ammonia=4:1:0.25)

EXAMPLE 23

4-(4-Benzyloxycarbonylamidino-phenyl)-1-methyl-2-[4-[2-(pivaloyloxymethyloxycarbonyl)-ethyl] -phenyl]-imidazole Prepared by reacting 4-(4-benzyloxycarbonylamidino-phenyl)-2-[4-(2-carboxy-ethyl)-phenyl]-1-methyl-imidazole with pivaloyloxymethylchloride in dimethylsulphoxide in the presence of potassium carbonate with the addition of potassium iodide at ambient temperature. The following compounds are obtained analogously:
(1) 4-(4-benzyloxycarbonylamidino-phenyl)-2-[4-[2-[(1 -ethoxycarbonyloxy-ethyl)-oxycarbonyl]-ethyl]-phenyl]-1-methyl-imidazole
(2) 4-(4-benzyloxycarbonylamidino-phenyl)-2-[4-[2-[(1 -cyclohexyloxycarbonyloxy-ethyl)-oxycarbonyl]-ethyl]-phenyl]-1-methyl-imidazole
(3) 2-[4-[2-(acetoxymethyloxycarbonyl)-ethyl]-phenyl]-4-(4 -benzyloxycarbonylamidino-phenyl)-1-methyl-imidazole
(4) 4-(benzyloxycarbonylamidino-phenyl)-2-[4-[2 -(butyryloxymethyloxycarbonyl)-ethyl]-phenyl]-1-methyl-imidazole
(5) 4-(benzyloxycarbonylamidino-phenyl)-2-[4-[2-(isobutyryloxymethyloxycarbonyl)-ethyl]-phenyl]-1-methyl-imidazole
(6) 2-[4-[2-(benzyloxymethyloxycarbonyl)-ethyl]-4-(4-benzyloxycarbonylamidino-phenyl)-1-methyl-imidazole (7) 1-[6-(4-benzyloxycarbonylamidino-phenyl)-3-pyridazinyl]-4-[2 -[(cyclohexyloxycarbonyloxymethyl)-oxycarbonyl]-ethyl]-imidazole (8) 2-(4-benzyloxycarbonylamidino-4'-biphenylyl)-5-[2-[(cyclohexyloxycarbonyloxymethyl)-oxycarbonyl]-ethyl]-1,3,4-thiadiazole (9) 1-[6-(4-benzyloxycarbonylamidino-phenyl)-3-pyridazinyl]-4-[2 -[(1-ethoxycarbonyloxy-ethyl)-oxycarbonyl]-ethyl]-imidazole

(10) 2-(4-benzyloxycarbonylamidino-4'-biphenylyl)-5-[2-[(1-ethoxycarbonyloxy-ethyl)-oxycarbonyl]-ethyl]-1,3,4-thiadiazole

(11) 1-[6-(4-benzyloxycarbonylamidino-phenyl)-3-pyridazinyl]-4 -[2-(pivaloyloxymethyloxycarbonyl)-ethyl]-imidazole

(12) 2-(4-Benzyloxycarbonylamidino-4'-biphenylyl)-5-[2 -(pivaloyloxymethyloxycarbonyl)-ethyl]-1,3,4-thiadiazole

EXAMPLE 24

4-(4-Diethylphosphorylamidino-phenyl)-2-[4-(2-methoxycarbonyl-ethyl)-phenyl]-1-methyl-imidazole Prepared by reacting 4-(4-amidino-phenyl)-2-[4-(2 -methoxycarbonyl-ethyl)-phenyl]-1-methyl-imidazole with diethylphosphorylcyanide in dimethylformamide.

EXAMPLE 25

Dry ampoule containing 2.5 mg of active substance per 1 ml
Composition:

| Active substance | 2.5 mg |
|---|---|
| Mannitol | 50.0 mg |
| Water for injections ad | 1.0 ml |

Preparation:

The active substance and mannitol are dissolved in water. After transferring the solution to the ampoule, it is freeze-dried.

At the point of use, the solution is made up with water for injections.

EXAMPLE 26

Dry ampoule containing 35 mg of active substance per 2 ml
Composition:

| Active substance | 35.0 mg |
|---|---|
| Mannitol | 100.0 mg |
| Water for injections ad | 2.0 ml |

Preparation:

The active substance and mannitol are dissolved in water. After transferring the solution to the ampoule, it is freeze-dried. At the point of use, the solution is made up with water for injections.

EXAMPLE 27

Tablet containing 50 mg of active substance
Composition:

| (1) Active substance | 50.0 mg |
|---|---|
| (2) Lactose | 98.0 mg |
| (3) Corn starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is mixed with the dried granules. From this mixture, compressed tablets are produced, biplanar, facetted on both sides and notched on one side. Diameter of tablets: 9 mm.

EXAMPLE 28

Tablet containing 350 mg of active substance
Composition:

| (1) Active substance | 350.0 mg |
|---|---|
| (2) Lactose | 136.0 mg |
| (3) Corn starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is mixed with the dried granules. From this mixture, compressed tablets are produced, biplanar, facetted on both sides and notched on one side. Diameter of tablets: 12 mm.

EXAMPLE 29

Capsules containing 50 mg of active substance
Composition:

| (1) Active substance | 50.0 mg |
|---|---|
| (2) Dried corn starch | 58.0 mg |
| (3) Powdered lactose | 50.0 mg |
| (4) Magnesium stearate | 2.0 mg |
| | 160.0 mg |

Preparation:

(1) is triturated with (3). This triturate is added to the mixture of (2) and (4), with thorough mixing. This powdered mixture is packed into size 3 hard gelatin oblong capsules in a capsule filling machine.

EXAMPLE 30

Capsules containing 350 mg of active substance
Composition:

| (1) Active substance | 300.0 mg |
|---|---|
| (2) Dried corn starch | 46.0 mg |

| | | |
|---|---|---|
| (3) Powdered lactose | 30.0 mg | |
| (4) Magnesium stearate | 4.0 mg | |
| | 430.0 mg | |

Preparation:

(1) is triturated with (3). This triturate is added to the mixture of (2) and (4), with thorough mixing. This powdered mixture is packed into size 0 hard gelatin oblong capsules in a capsule filling machine.

What is claimed is:

1. A tetrazole of the formula

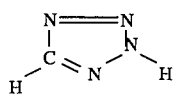

wherein one of the two hydrogen atoms is replaced by a group of the formula $R^A$—$R^B$—$R^C$— in which $R^A$ represents an amino group, an aminoalkyl group with 1 to 3 carbon atoms, an amidino or guanidino group, wherein in the before mentioned groups an amino or imino group may be substituted by an alkoxycarbonyl group or by a phenylalkoxy group, wherein each of the alkoxy moieties may contain 1 to 3 carbon atoms, or a cyano group, $R^B$ represents a bond, a phenylene group which may be substituted by a fluorine, chlorine or bromine atom, by an alkyl or alkoxy group, wherein the alkyl and alkoxy moiety may each contain 1 to 3 carbon atoms, a pyridinylene, pyrimidinylene, pyrazinylene or pyridazinylene group, wherein one or two —CH=N— groups may each be replaced by a —CO—NR$_1$— group, wherein R$_1$ represents a hydrogen atom or an alkyl group containing 1 to 3 carbon atoms, and $R^C$ represents a phenylene group which may be substituted by fluorine, chlorine or bromine atom, by an alkyl, alkoxy, alkylsulphenyl, alkylsulphinyl or alkylsulphonyl group, wherein each alkyl or alkoxy moiety may contain 1 to 3 carbon atoms, a pyridinylene, pyrimidinylene, pyrazinylene or pyridazinylene group optionally substituted by an alkyl group with 1 to 3 carbon atoms, wherein one or two —CH=N— groups may each be replaced by a —CO—NR$_1$— group, wherein R$_1$ is defined as hereinbefore, a cyclohexylene group wherein one or two CH units may be replaced by a nitrogen atom, an indanylene or 1,2,3,4-tetrahydro-naphthylene group wherein the saturated ring is bound to group $R^A$ and the unsaturated ring is bound to the tetrazole nucleus;

and the other hydrogen atom is replaced by a group of the formula $R^F$—$R^E$—$R^D$—, in which $R^D$ represents an alkylene group containing 1 to 3 carbon atoms, a phenylene group which may be substituted by a fluorine, chlorine or bromine atom, by an alkyl, hydroxy, alkoxy, alkylsulphenyl, alkylsulphinyl, alkylsulphonyl, nitro, amino, alkylcarbonylamino, alkylsulphonylamino, carboxyalkoxy, alkoxycarbonylalkoxy or benzamido group, wherein each alkyl or alkoxy moiety may contain 1 to 3 carbon atoms and the phenyl group of the benzamido group may be substituted by a chlorine or bromine atom or by an alkyl or alkoxy group each containing 1 to 3 carbon atoms, a pyridinylene, pyrimidinylene, pyrazinylene or pyridazinylene group, wherein one or two —CH=N— groups may each be replaced by a —CO—NR$_1$— group, wherein R$_1$ is defined as hereinbefore, or a cyclohexylene group wherein one or two CH units may be replaced by a nitrogen atom, $R^E$ represents a bond, a straight chained or branched C$_{1-4}$-alkylene group, an alkenylene group with 2 to 4 carbon atoms, or an alkylene group with 1 to 3 carbon atoms linked to the group $R^D$ via an oxygen or sulphur atom, a sulphinyl, sulphonyl, imino or (alkylcarbonyl)imino group, wherein the alkyl moiety may contain 1 to 3 carbon atoms, and $R^F$ represents a carbonyl group which is substituted by a hydroxy group, by an amino group, by an alkoxy group with 1 to 5 carbon atoms, by a cycloalkoxy group with 3 to 7 carbon atoms or by an alkanoyloxy-methoxy group having a total of 2 to 6 carbon atoms in the alkanoyl moiety, by an alkoxycarbonyloxy-methoxy group having 1 to 6 carbon atoms in the alkoxy moiety, by a cycloalkanoyloxy-methoxy group having a total 4 to 8 carbon atoms in the cycloalkanoyl moiety, wherein the methoxy moiety may be substituted by a methyl group, or $R^F$ may represent a phosphono group, a O-alkyl-phosphono or O,O'-dialkyl-phosphono group containing in each alkyl moiety 1 to 3 carbon atoms, or a tautomer or pharmaceutically acceptable salt thereof.

2. A compound as claimed in claim 1, wherein $R^A$ represents an amidino group optionally substituted by an alkoxycarbonyl group, wherein the alkoxy moiety may contain 1 to 3 carbon atoms, a cyano or aminomethyl group, $R^B$ represents a bond, a phenylene group which may be substituted by a fluorine, chlorine or bromine atom, by a methyl or methoxy group, a pyridinylene, pyrimidinylene, pyrazinylene or pyridazinylene group, $R^C$ represents a phenylene group which may be substituted by a fluorine, chlorine or bromine atom, by a methyl, methoxy, methylsulphenyl, methylsulphinyl or methylsulphonyl group, a pyridinylene, pyrimidinylene, pyrazinylene or pyridazinylene group, a cyclohexylene group wherein one CH unit may be replaced by a nitrogen atom, $R^D$ represents an alkylene group containing 1 to 3 carbon atoms, a phenylene group which may be substituted by a fluorine, chlorine or bromine atom, by a methyl, hydroxy, methoxy, methylsulphenyl, methylsulphinyl, methylsulphonyl, nitro, amino, acetamido, benzamido, methanesulfonylamido, carboxymethoxy or methoxycarbonylmethoxy group, a pyridinylene, pyrimidinylene, pyrazinylene or pyridazinylene group, or a cyclohexylene group wherein one CH unit may be replaced by a nitrogen atom, $R^E$ represents a bond, a straight chained or branched $C_{1-4}$-alkylene group, an alkenylene group with 2 to 4 carbon atoms, or a methylene group linked to the group $R^D$ via an oxygen or sulphur atom, a sulphenyl, sulphinyl, sulphonyl, imino or (acetyl)imino group, and $R^F$ represents a carbonyl group which is substituted by a hydroxy group, by an alkoxy group with 1 to 4 carbon atoms or by a pivaloyloxy-methoxy group, or a tautomer or pharmaceutically acceptable salt thereof.

3. A compound as claimed in claim 1, wherein $R^A$ represents an amidino group optionally substituted by an alkoxycarbonyl group, wherein the alkoxy moiety may contain 1 to 3 carbon atoms, $R^B$ represents a bond, a phenylene or pyridinylene group, and $R^C$ represents a phenylene group, or a cyclohexylene group wherein one CH unit attached to group $R^B$ is replaced by a nitrogen atom, $R^D$ represents an ethylene group, or a phenylene group, $R^E$ represents a bond or an ethylene group, and $R^F$ represents a carbonyl group which is substituted by a hydroxy group or by an alkoxy group with 1 to 3 carbon atoms, or a tautomer or pharmaceutically acceptable salt thereof.

4. 5-(4-amidino-phenyl)-2-[4-(2-carboxy-ethyl)-phenyl]-tetrazole or a pharmaceutically acceptable salt thereof.

5. 5-(4-amidino-4'-biphenylyl)-2-(2-carboxy-ethyl)-tetrazole or a pharmaceutically acceptable salt thereof.

6. 5-(4-amidino-4'-biphenylyl)-2-(2-methoxycarbonyl-ethyl)tetrazole or a pharmaceutically acceptable salt thereof.

7. 5-[1-(4-amidino-phenyl)-4-piperidinyl]-2-[4-(2-carboxyethyl)-phenyl]-tetrazole or pharmaceutically acceptable salt thereof.

8. 5-[1-(5-amidino-2-pyridyl)-4-piperidinyl]-2-[4-(2-carboxyethyl)-phenyl]-tetrazole or a pharmaceutically acceptable salt thereof.

9. 5-[1-(4-amidino-phenyl)-4-piperidinyl]-2-[4-(2-methoxycarbonyl-ethyl)-phenyl]-tetrazole or a pharmaceutically acceptable salt thereof.

10. 5-[1-(5-amidino-2-pyridyl)-4-piperidinyl]-2-[4-(2-methoxycarbonyl-ethyl)phenyl]-tetrazole or a pharmaceutically acceptable salt thereof.

11. 5-(4-amidino-phenyl)-2-[4-(2-methoxycarbonyl-ethyl)-phenyl]-tetrazole or a pharmaceutically acceptable salt thereof.

12. 5-(4-methoxycarbonylamidino-4'-biphenylyl)-2-(2-methoxycarbonyl-ethyl)-tetrazole or a pharmaceutically acceptable salt thereof.

* * * * *